(12) United States Patent
Ham et al.

(10) Patent No.: US 12,174,140 B2
(45) Date of Patent: Dec. 24, 2024

(54) ELECTRONIC CIRCUITS FOR ANALYZING ELECTROGENIC CELLS AND RELATED METHODS

(71) Applicant: President and Fellows of Harvard College, Cambridge, MA (US)

(72) Inventors: Donhee Ham, Cambridge, MA (US); Hongkun Park, Cambridge, MA (US); Keith Krenek, Cambridge, MA (US); Tianyang Ye, Cambridge, MA (US); Jeffrey T. Abbott, Cambridge, MA (US); Wenxuan Wu, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 519 days.

(21) Appl. No.: 16/760,723

(22) PCT Filed: Oct. 30, 2018

(86) PCT No.: PCT/US2018/058081
§ 371 (c)(1),
(2) Date: Apr. 30, 2020

(87) PCT Pub. No.: WO2019/089495
PCT Pub. Date: May 9, 2019

(65) Prior Publication Data
US 2020/0292482 A1    Sep. 17, 2020

Related U.S. Application Data

(60) Provisional application No. 62/580,126, filed on Nov. 1, 2017.

(51) Int. Cl.
*G01N 27/327* (2006.01)
*C12M 1/34* (2006.01)
(Continued)

(52) U.S. Cl.
CPC .......... *G01N 27/327* (2013.01); *C12M 41/00* (2013.01); *C12N 13/00* (2013.01); *G01N 27/416* (2013.01)

(58) Field of Classification Search
CPC .............. G01N 27/327; G01N 27/416; G01N 33/5438; G01N 33/6872; C12M 41/00;
(Continued)

(56) References Cited

U.S. PATENT DOCUMENTS 5,072,194 A * 12/1991 Chevallier .......... H03F 3/45103
330/294
5,233,985 A * 8/1993 Hudrlik ................... A61N 1/37
607/27
(Continued)

FOREIGN PATENT DOCUMENTS

DE     19529371 C2     1/1998
EP     1271144 A1 *   1/2003   ....... G01N 33/48728
(Continued)

OTHER PUBLICATIONS

Jorgolli M., Integrated Nanoscale Tools for Interrogating Living Cells, PhD thesis, Harvard University, 2015 (Year: 2015).*
(Continued)

*Primary Examiner* — Luan V Van
*Assistant Examiner* — Shizhi Qian
(74) *Attorney, Agent, or Firm* — Wolf, Greenfield & Sacks, P.C.

(57) ABSTRACT

Methods and systems for monitoring the activity of electrogenic networks are described. One representative system includes an array of electrode coupled to an analyzer having a stimulator and a receiver. The electrode is placed in contact with an electrogenic cell. The electrodes can be shaped as nanowires, tubes, cavities and/or cones. The analyzer may be configured to operate in a voltage stimulation mode, in
(Continued)

which the cells are stimulated via voltages and monitored via current, or in a current stimulation mode, in which the cells are stimulated via currents and monitored via voltages. The analyzers may be arranged as single-stage amplifiers, and may include a feedback loop shared between the stimulation signal path and the sensing signal path. The feedback loop may be arranged to provide overlapping stimulation and sensing of the electrogenic network's cells.

18 Claims, 25 Drawing Sheets

(51) Int. Cl.
  *C12N 13/00* (2006.01)
  *G01N 27/416* (2006.01)
(58) Field of Classification Search
  CPC ........ C12N 13/00; A61N 1/0551; A61N 1/02; A61N 1/04; A61N 1/18
  See application file for complete search history.

(56) References Cited

U.S. PATENT DOCUMENTS

| | | | |
|---|---|---|---|
| 5,605,612 A | 2/1997 | Park et al. | |
| 7,332,313 B2 | 2/2008 | Giaever et al. | |
| 8,159,300 B2 | 4/2012 | Masuda et al. | |
| 8,227,223 B2 | 7/2012 | Giaever et al. | |
| 9,121,806 B1 | 9/2015 | Bhansali et al. | |
| 9,360,469 B1 | 6/2016 | Clements et al. | |
| 9,700,221 B2 | 7/2017 | Rajaraman et al. | |
| 9,983,198 B2 | 5/2018 | Chvatal et al. | |
| 11,167,131 B2 | 11/2021 | Isaacs et al. | |
| 11,747,321 B2 | 9/2023 | Ham et al. | |
| 11,768,196 B2 | 9/2023 | Ham et al. | |
| 11,774,396 B2 | 10/2023 | Ham et al. | |
| 11,833,346 B2 | 12/2023 | Park et al. | |
| 2002/0010415 A1* | 1/2002 | Simon ............... A61K 49/0002 | 604/20 |
| 2002/0045318 A1 | 4/2002 | Chen et al. | |
| 2002/0190732 A1 | 12/2002 | Cheng et al. | |
| 2003/0100189 A1 | 5/2003 | Lee et al. | |
| 2004/0100290 A1 | 5/2004 | Pope et al. | |
| 2005/0170510 A1 | 8/2005 | Huang et al. | |
| 2005/0253137 A1* | 11/2005 | Whang ............... H01L 29/0673 | 257/40 |
| 2005/0282284 A1 | 12/2005 | Rubinsky et al. | |
| 2006/0121446 A1* | 6/2006 | Abassi ............... C12M 35/02 | 435/456 |
| 2007/0043301 A1 | 2/2007 | Martisen et al. | |
| 2007/0072257 A1 | 3/2007 | Negulescu et al. | |
| 2007/0087401 A1 | 4/2007 | Neilson et al. | |
| 2007/0187840 A1 | 8/2007 | Dell'Acqua-Bellavitis et al. | |
| 2007/0264634 A1 | 11/2007 | Bock et al. | |
| 2008/0009434 A1 | 1/2008 | Reches et al. | |
| 2008/0218939 A1 | 9/2008 | Marcus et al. | |
| 2009/0146735 A1* | 6/2009 | Jeong ............... H03F 3/005 | 327/554 |
| 2009/0227066 A1 | 9/2009 | Joseph et al. | |
| 2009/0255801 A1 | 10/2009 | Hass | |
| 2010/0164110 A1 | 7/2010 | Jin et al. | |
| 2010/0304425 A1 | 12/2010 | Speller | |
| 2011/0210718 A1 | 9/2011 | Vana et al. | |
| 2011/0233512 A1 | 9/2011 | Yang et al. | |
| 2011/0253982 A1 | 10/2011 | Wang et al. | |
| 2012/0094328 A1 | 4/2012 | Park et al. | |
| 2012/0157804 A1 | 6/2012 | Rogers et al. | |
| 2012/0182168 A1* | 7/2012 | Shibata ............... H03H 11/1291 | 327/552 |
| 2013/0041235 A1 | 2/2013 | Rogers et al. | |
| 2013/0072775 A1 | 3/2013 | Rogers et al. | |
| 2013/0115705 A1 | 5/2013 | Patolsky et al. | |
| 2013/0123136 A1 | 5/2013 | Abassi et al. | |
| 2013/0260467 A1 | 10/2013 | Park et al. | |
| 2013/0338746 A1 | 12/2013 | Guvanasen et al. | |
| 2013/0341734 A1 | 12/2013 | Merz | |
| 2014/0001041 A1 | 1/2014 | Rahman et al. | |
| 2014/0057283 A1 | 2/2014 | Wang et al. | |
| 2015/0005680 A1* | 1/2015 | Lipani ............... A61F 7/12 | 607/113 |
| 2015/0027885 A1 | 1/2015 | Rajaraman et al. | |
| 2015/0148863 A1 | 5/2015 | Yun et al. | |
| 2015/0376811 A1* | 12/2015 | Joung ............... C25D 13/18 | 524/588 |
| 2015/0377856 A1* | 12/2015 | Dunbar ............... G01N 33/48728 | 204/452 |
| 2016/0047770 A1 | 2/2016 | Tyler et al. | |
| 2016/0096173 A1 | 4/2016 | Teich et al. | |
| 2016/0245790 A1 | 8/2016 | Kawai et al. | |
| 2016/0278713 A1* | 9/2016 | Shoaran ............... A61B 5/7232 | |
| 2017/0058246 A1 | 3/2017 | Grier, Jr. et al. | |
| 2017/0176414 A1 | 6/2017 | Abdolahad et al. | |
| 2017/0336384 A1 | 11/2017 | Ino et al. | |
| 2018/0163165 A1 | 6/2018 | Grier, Jr. et al. | |
| 2018/0169403 A1 | 6/2018 | Park et al. | |
| 2018/0246079 A1 | 8/2018 | Wang et al. | |
| 2020/0064336 A1 | 2/2020 | Zafar et al. | |
| 2021/0187280 A1 | 6/2021 | Park et al. | |
| 2021/0236033 A1 | 8/2021 | Butera et al. | |
| 2021/0371846 A1 | 12/2021 | Ham et al. | |
| 2022/0397512 A1 | 12/2022 | Ham et al. | |
| 2023/0014082 A1 | 1/2023 | Ham et al. | |
| 2023/0184739 A1 | 6/2023 | Ham et al. | |

FOREIGN PATENT DOCUMENTS

| | | | |
|---|---|---|---|
| JP | 2008269725 A * | 11/2008 | |
| WO | WO-2009137440 A1 * | 11/2009 | ............. G01N 27/02 |
| WO | WO 2012/050876 | 4/2012 | |
| WO | WO 2012/050881 | 4/2012 | |
| WO | WO 2016/112315 | 7/2016 | |
| WO | WO-2016112315 A2 * | 7/2016 | ............... A61N 1/05 |
| WO | WO 2019/010343 A1 | 1/2019 | |
| WO | WO 2021/257686 A1 | 12/2021 | |
| WO | WO 2021/257701 A1 | 12/2021 | |
| WO | WO 2021/257705 A1 | 12/2021 | |

OTHER PUBLICATIONS

Giovangrandi et al., Low-cost microelectrode array wit integrated heater for extracellular recording of cardiomyocyte cultures using commercial flexible printed circuit technology, Sensors and Actuators B, 2006, 113., 545-554. (Year: 2006).*
U.S. Appl. No. 15/542,197, filed Jul. 7, 2017, Park et al.
PCT/US2016/012685, Feb. 24, 2016, Invitation to Pay Additional Fees.
PCT/US2016/012685, May 3, 2016, International Search Report and Written Opinion.
PCT/US2016/012685, Jul. 20, 2017, International Preliminary Report on Patentability.
PCT/US18/58081, Jan. 15, 2019, Invitation to Pay Additional Fees.
PCT/US18/58081, Mar. 22, 2019, International Search Report and Written Opinion.
PCT/US18/58081, May 14, 2019, International Preliminary Report on Patentability.
PCT/US18/40969, Aug. 31, 2018, Invitation to Pay Additional Fees.
PCT/US18/40969, Nov. 2, 2018, International Search Report and Written Opinion.
PCT/US18/40969, Jan. 16, 2020, International Preliminary Report on Patentability.
International Search Report and Written Opinion mailed Sep. 29, 2021 for Application No. PCT/US2021/037604.
International Search Report and Written Opinion mailed Sep. 22, 2021 for Application No. PCT/US2021/037626.
International Search Report and Written Opinion mailed Sep. 28, 2021 for Application No. PCT/US2021/037630.
Kim et al., An area-efficient low-noise CMOS DNA detection sensor for multichannel nanopore applications. Sensors and Actuators B: Chemical. Jan. 2013;176:1051-1055.

(56) References Cited

OTHER PUBLICATIONS

Invitation to Pay Additional Fees for Application No. PCT/US2016/012685 mailed Feb. 24, 2016.
International Search Report and Written Opinion for Application No. PCT/US2016/012685 mailed May 3, 2016.
International Preliminary Report on Patentability for PCT/US2016/012685 mailed Jul. 20, 2017.
Invitation to Pay Additional Fees for Application No. PCT/US18/58081 mailed Jan. 1, 2019.
International Search Report and Written Opinion for Application No. PCT/US18/58081 mailed Mar. 22, 2019.
International Preliminary Report on Patentability for Application No. PCT/US18/58081 mailed May 14, 2020.
Invitation to Pay Additional Fees for Application No. PCT/US18/40969 mailed Aug. 31, 2018.
International Search Report and Written Opinion for Application No. PCT/US18/40969 mailed Nov. 2, 2018.
International Preliminary Report on Patentability for Application No. PCT/US18/40969 mailed Jan. 16, 2020.
Crescentini et al., Noise limits of CMOS current interfaces for biosensors: a review. IEEE Trans Biomed Circuits Syst. 2014;8(2):278-292.
International Preliminary Report on Patentability for Application No. PCT/US2021/037604 mailed Dec. 29, 2022.
International Preliminary Report on Patentability for Application No. PCT/US2021/37626 mailed Dec. 29, 2022.
International Preliminary Report on Patentability No. PCT/US2021/037630 mailed Dec. 29, 2022.
Abbott et al., CMOS nanoelectrode array for all-electrical intracellular electrophysiological imaging. Nat Nanotechnol. May 2017;12(5):460-466. doi: 10.1038/nnano.2017.3. Epub Feb. 13, 2017.
Abbott et al., Multi-parametric functional imaging of cell cultures and tissues with a CMOS microelectrode array. Lab Chip. Mar. 29, 2022;22(7):1286-1296. doi: 10.1039/d1lc00878a.
Laborde et al., Real-time imaging of microparticles and living cells with CMOS nanocapacitor arrays. Nat Nanotechnol. Sep. 2015;10(9):791-5. doi: 10.1038/nnano.2015.163. Epub Aug. 3, 2015.
Park et al., 1024-Pixel CMOS Multimodality Joint Cellular Sensor/Stimulator Array for Real-Time Holistic Cellular Characterization and Cell-Based Drug Screening. IEEE Trans Biomed Circuits Syst. Feb. 2018; 12(1): 80-94. Author manuscript provided. 45 pages.
U.S. Appl. No. 17/144,387, filed Jan. 8, 2021, Park et al.
U.S. Appl. No. 17/891,964, filed Aug. 19, 2022, Ham et al.
U.S. Appl. No. 17/877,702, filed Jul. 29, 2022, Ham et al.
U.S. Appl. No. 17/940,174, filed Sep. 8, 2022, Ham et al.
U.S. Appl. No. 16/625,603, filed Dec. 20, 2019, Abbott et al.
PCT/US2021/037604, Dec. 29, 2022, International Preliminary Report on Patentability.
PCT/US2021/37626, Dec. 29, 2022, International Preliminary Report on Patentability.
PCT/US2021/037630, Dec. 29, 2022, International Preliminary Report on Patentability.

\* cited by examiner

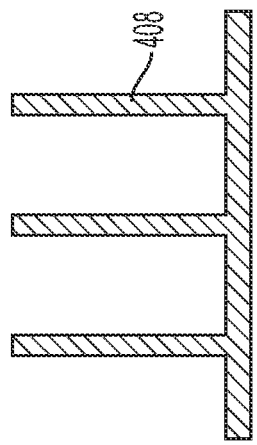
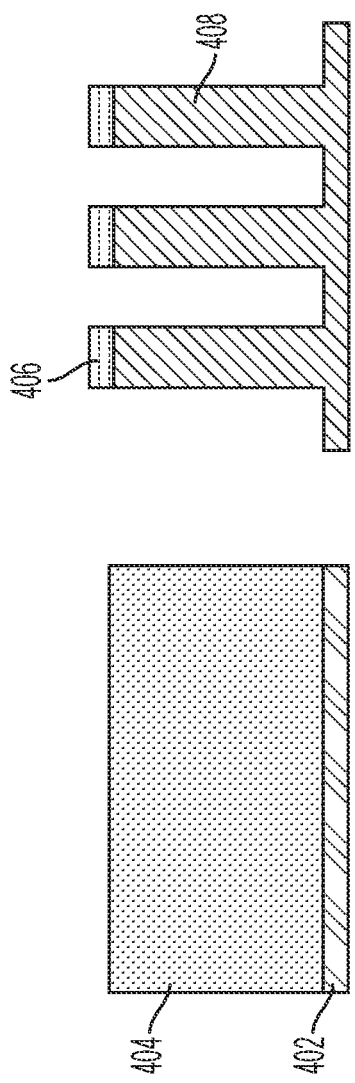
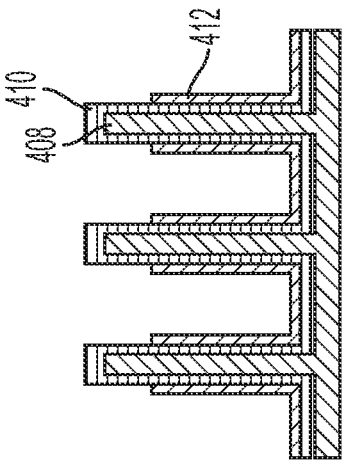
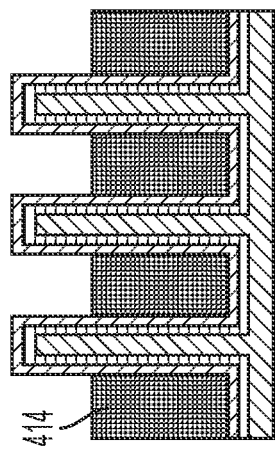
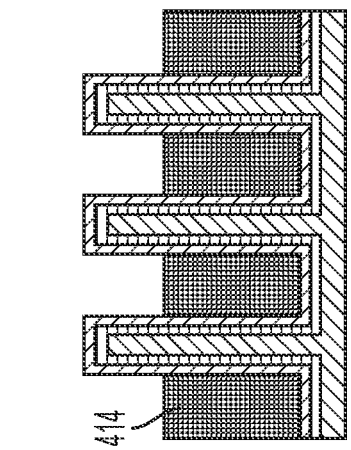
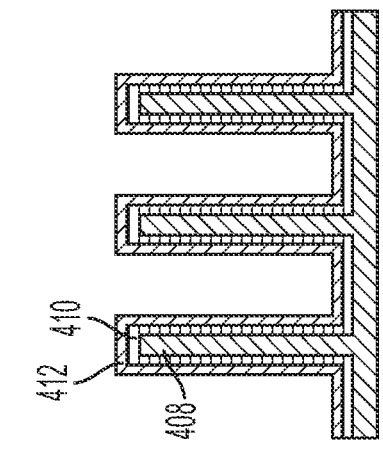

ELECTRONIC CIRCUITS FOR ANALYZING ELECTROGENIC CELLS AND RELATED METHODS

RELATED APPLICATIONS

The present application is a national stage filing under 35 U.S.C. § 371 of International Patent Application Serial No. PCT/US2018/058081, filed Oct. 30, 2018, which claims the benefit under 35 U.S.C. § 119(e) of U.S. Provisional Patent Application Ser. No. 62/580,126 entitled "ELECTRONIC CIRCUITS FOR ANALYZING ELECTROGENIC CELLS AND RELATED METHODS," filed Nov. 1, 2017, each of which is incorporated herein by reference in its entirety.

GOVERNMENT FUNDING

This invention was made with government support under MH105960 awarded by the National Institutes of Health, and W911NF-15-1-0565, W911NF-15-1-0548, and W911NF-17-1-0425 awarded by the U.S. Army/Army Research Office. The government has certain rights in the invention.

BACKGROUND

To date, many neurological disorders remain poorly understood and lack therapeutic treatments despite research programs focusing on elucidating the cellular basis of the disorders and screening for potential new drugs. In part, this has been attributed to a shortage of drug screening assays that facilitate large-scale experiments with primary mammalian neurons.

Over the course of the last two decades, drugs targeting both voltage- and ligand-gated ion channels have been successfully developed to treat a broad range of neurological diseases. Despite their validated potential as druggable targets, ion-channel-targeted drug discovery has experienced slow progress in large part due to the experimental difficulty in evaluating their interaction with novel compounds. Genome-wide association studies continue to identify ion channel mutations that result in ion channel irregularities, which contribute to many debilitating diseases including Parkinson's Disease, Alzheimer's Disease, hyperactivity disorders, epilepsy, and autism. The constantly increasing rate of discovery of new candidate targets necessitates high-throughput techniques to evaluate their efficacy as therapeutic targets.

The need for high-throughput ion channel screening has spurred the development of several methods based on indirect measurement of ion channel activity, such as ion-flux assays and cell-based assays with membrane potential- or $Ca^{2+}$-sensitive dyes. Although these methods have become an integral part of ion channel drug discovery efforts, electrophysiological measurements that directly monitor the electric activity of ion channels remain the benchmark assay for confirmation of compound activity and efficacy. However, electrophysiological measurements have been of limited utility in drug screening efforts in large part due to their labor-intensive and low-throughput nature. To address this drawback, automated planar-patch electrophysiology platforms have been developed, allowing for higher throughput drug screening experiments. Although planar-patch platforms have proven useful in several drug discovery programs including identification and optimization efforts, their application is limited to large cells and stable cell lines designed to express the channel of interest. However, the process of stably expressing cell lines is costly, time-consuming, and often associated with low viability. In addition, characterization of the compound's activity in dissociated cells does not warrant the same effect in a complex neuronal network. Automated planar-patch platforms are limited not only by their poor performance with primary mammalian neurons and neuronal cultures, but also by their unsuitability of recording from connected pairs of neurons.

Nanowires (NWs) provide a powerful new system for determining electrical conditions within cells, or applying electrical forces to cells. However, due to their size, typically on the order of nanometers, it is difficult to expose arrays of nanowires and cells to different conditions. Accordingly, improvements are needed.

BRIEF SUMMARY

Some embodiments relate to an apparatus for analyzing an electrogenic cell, the apparatus may comprise an array of electrodes and a control circuit coupled to at least one electrode of the array of electrodes. The control circuit may comprise a current generator configured to drive the at least one electrode with an electrical current and an amplifier capacitively coupled the current generator and arranged in a negative feedback configuration.

In some embodiments, the at least one electrode is coupled to a non-inverting input terminal of the amplifier.

In some embodiments, the control circuit comprises an impedance element coupled between an inverting input terminal of the amplifier and an output terminal of the amplifier, wherein the impedance element has an impedance that is larger than 1 G$\Omega$.

In some embodiments, the at least one electrode is covered, at least in part, with a material having a nanoscale roughness.

In some embodiments, the apparatus further comprises a temperature sensor and a heater disposed adjacent the array of electrodes.

In some embodiments, the at least one electrode is electrically in contact with the electrogenic cell.

In some embodiments, the at least one electrode is shaped as a nanowire.

Some embodiments relate to a method for analyzing an electrogenic cell, the method comprising driving, with a current generator, an electric current through an electrode that is electrically in contact with the electrogenic cell; and receiving a voltage generated by the electrogenic cell with an amplifier arranged in a feedback configuration and capacitively coupled to the current generator.

In some embodiments, the method further comprises providing a negative feedback signal between an inverting input terminal of the amplifier and an output terminal of the amplifier via an impedance element having an impedance that is larger than 1 G$\Omega$.

In some embodiments, the method further comprises controlling a temperature of the electrogenic cell using a heather disposed adjacent the electrode.

In some embodiments, driving the electric current through the electrode and receiving the voltage generated by the electrogenic cell are performed in overlapping phases.

Some embodiments relate to an apparatus for analyzing an electrogenic cell, the apparatus comprising: an array of electrodes and a control circuit coupled to at least one electrode of the array of electrodes. The control circuit may comprise an amplifier arranged in a negative feedback configuration and configured to drive the at least one electrode with a reference voltage; and convert a current received from the electrogenic cell through the at least one electrode into an output voltage.

In some embodiments, the at least one electrode is coupled to a non-inverting input terminal of the amplifier.

In some embodiments, the control circuit comprises an impedance element coupled between an inverting input terminal of the amplifier and an output terminal of the amplifier, wherein the impedance element has an impedance that is larger than 1 GΩ.

In some embodiments, the at least one electrode is covered, at least in part, with a material having a nanoscale roughness.

In some embodiments, the array of electrodes has a pitch that is less than 40 μm.

In some embodiments, the apparatus further comprises a temperature sensor and a heater disposed adjacent the array of electrodes.

In some embodiments, the at least one electrode is electrically in contact with the electrogenic cell.

Some embodiments relate to a method for analyzing an electrogenic cell, the method comprising driving, with an amplifier arranged in a feedback configuration, an electrode electrically in contact with the electrogenic cell with a reference voltage; and converting a current received from the electrogenic cell through the at least one electrode into an output voltage with the amplifier.

In some embodiments, the method further comprises providing a negative feedback signal between an inverting input terminal of the amplifier and an output terminal of the amplifier via an impedance element having an impedance that is larger than 1 GΩ.

In some embodiments, the method further comprises controlling a temperature of the electrogenic cell using a heater disposed adjacent the electrode.

Some embodiments relate to a method of fabricating an apparatus for analyzing an electrogenic cell, the method comprising forming an array of electrodes; forming a control circuit comprising a current generator configured to drive at least one electrode of the array of electrodes with an electrical current and an amplifier capacitively coupled the current generator and arranged in a negative feedback configuration.

In some embodiments, forming the array of electrodes comprises forming a plurality of dielectric pillars using a lithographic process; sputtering metal to cover the plurality of dielectric pillars; partially covering, with platinum black, the plurality of dielectric pillars covered with the metal.

In some embodiments, forming the array of electrodes comprises forming a well having sidewalls made of a dielectric material; sputtering metal to cover an inner portion of the sidewalls; filling the well with photoresist; forming a hole though the photoresist; dissolving, at least partially, the photoresist through the hole; and covering the metal, at least partially, with platinum black.

Some embodiments relate to an apparatus for analyzing a plurality of electrogenic cells, the apparatus comprising: a plurality of electrodes comprising a first electrode configured to be in electrical communication with a first electrogenic cell of the plurality of electrogenic cells and a second electrode configured to be in electrical communication with a second electrogenic cell of the plurality of electrogenic cells; an integrated circuit (IC) coupled to the plurality of electrodes. The IC may comprise a first stimulator coupled to the first electrode and configured to electrically stimulate, with a first stimulus signal, the first electrogenic cell and a second stimulator coupled to the second electrode and configured to electrically stimulate, with a second stimulus signal, the second electrogenic cell; a first receiver coupled to the first electrode and configured to sense a response to the first stimulus signal of the first electrogenic cell and a second receiver coupled to the second electrode and configured to sense a response to the second stimulus signal of the second electrogenic cell; and control circuitry configured to control at least one timing characteristic of the first stimulus signal and at least one timing characteristic of the second stimulus signal.

In some embodiments, the control circuitry is configured to control a duration of the first stimulus signal and a duration of the second stimulus signal.

In some embodiments, the control circuitry is configured to control a delay of the first stimulus signal and a delay of the second stimulus signal.

In some embodiments, the IC further comprises a first switch coupled between the first stimulator and the second receiver, and wherein the control circuitry is configured to control a state of the first switch to enable or disable communication between the first stimulator and the second receiver.

In some embodiments, the IC further comprises a second switch coupled between the first stimulator and the first receiver, and wherein the control circuitry is configured to control a state of the second switch to enable or disable communication between the first stimulator and the first receiver.

In some embodiments, the plurality of electrodes comprises a plurality of nanowires.

In some embodiments, the IC comprises a silicon substrate.

Some embodiments relate to a method for analyzing a plurality of electrogenic cells, the method comprising: electrically stimulating a first electrogenic cell of the plurality of electrogenic cells by generating, using a first stimulator disposed on an integrated circuit (IC), a first stimulus signal; electrically stimulating a second electrogenic cell of the plurality of electrogenic cells by generating, using a second stimulator disposed on the IC, a second stimulus signal; sensing, using a first receiver disposed on the IC, a response to the first stimulus of the first electrogenic cell; sensing, using a second receiver disposed on the IC, a response to the second stimulus of the second electrogenic cell; and controlling, using control circuitry disposed on the IC, at least one timing characteristic of the first stimulus signal and at least one timing characteristic of the second stimulus signal.

In some embodiments, controlling at least one timing characteristic of the first stimulus signal comprises controlling a duration of the first stimulus signal and controlling at least one timing characteristic of the second stimulus signal comprises controlling a duration of the second stimulus signal In some embodiments, controlling at least one timing characteristic of the first stimulus signal comprises controlling a delay of the first stimulus signal and controlling at least one timing characteristic of the second stimulus signal comprises controlling a delay of the second stimulus signal Some embodiments relate to a method for forming arbitrary biological connection among a plurality of electrogenic cells, the method comprising enhancing or weakening respective biological connections between first and second electrogenic cells of the plurality of electrogenic cells using an integrated circuit (IC).

In some embodiments, enhancing or weakening respective connections between first and seconds electrogenic cells of the plurality of electrogenic cells comprises adjusting a duration of a stimulus signal relative to an activation interval of the plurality of electrogenic cells.

In some embodiments, the method further comprises setting the duration of the stimulus signal outside the activation interval to strengthen at least one biological connection.

In some embodiments, the method further comprises setting the duration of the stimulus signal within the activation interval to weaken at least one biological connection.

BRIEF DESCRIPTION OF THE DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

FIGS. 4A-4F collectively illustrate a representative process for fabricating a plurality of nanowires, according to some non-limiting embodiments.

DETAILED DESCRIPTION

I. Overview

Figure 1A:
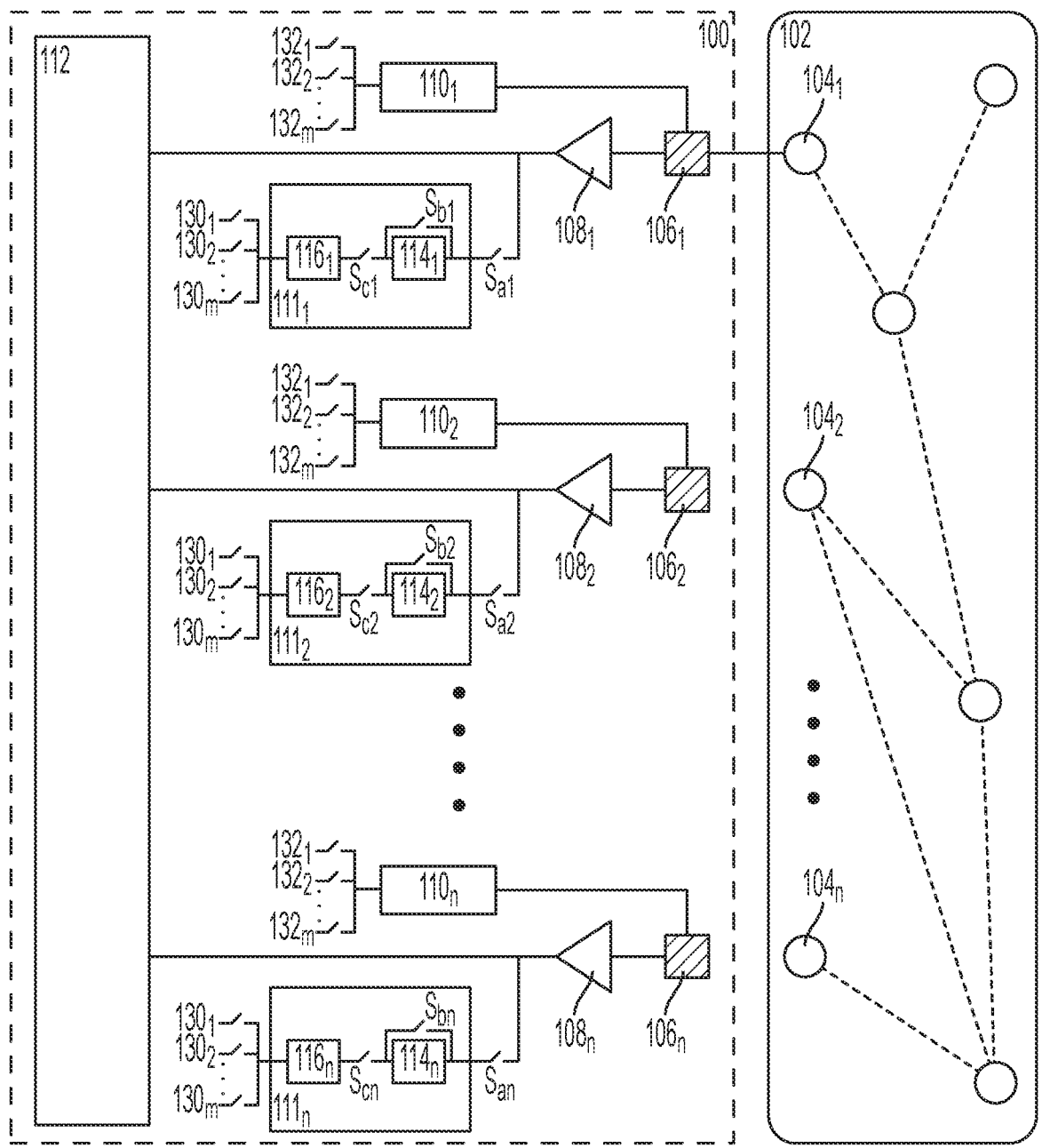
FIG. 1A is schematic diagram illustrating an electrogenic network and a probing system, according to some non-limiting embodiments.

The inventors have recognized and appreciated that the ability to analyze the electrical activity of electrogenic cells may be enhanced by using control circuits that can stimulate the electrogenic cells and receive response signals from the electrogenic cells in overlapping phases (e.g., simultaneously). Accordingly, the inventors have appreciated that conventional systems designed to stimulate the electrogenic cells during a first phase and then receive the response from the cells during a second phase, exhibit limited abilities to discern certain types of electrical activity from others.

Electrogenic cells are biological cells that are capable of generating and/or responding to electric signals. Electrogenic cells can be arranged in networks, where the cells communicate with other cells of the network via electric signals (referred to herein also as bioelectric events). Examples of electrogenic cells include, but are not limited to, brain cells, heart cells, endocrine cells, and other muscular cells. Action potentials are one example of these electric signals. Action potentials occur in several types of biological cells and can be generated by special types of voltage-gated ion channels embedded in a cell's plasma membrane. These channels may be shut when the membrane potential is near the resting potential of the cell, and may be opened if the membrane increases to a precisely defined threshold voltage.

Some embodiments of the present disclosure are directed to systems configured to stimulate electronic cells and record the activity resulting from the stimulation in overlapping phases (e.g., simultaneously). In some embodiments, electric current may be used to stimulate the cells, and the voltage resulting in the cells from the stimulation is analyzed. Systems of this type operate in the so-called "current stimulation mode." By contrast, in other embodiments, the cells may be stimulated through voltages, and the electric currents provided by the cells in response to the stimulation are analyzed. Systems of this type operate in the so-called "voltage stimulation mode."

The inventors have further recognized and appreciated that the ability to analyze electrogenic cells' electrical activity can be significantly increased by increasing the number of cells that are stimulated using a single probing system. In some embodiments, this can be accomplished by increasing the number of analyzers integrated on a single probing system. According to one aspect of the present disclosure, the number of analyzers in a single system is increased, relative to conventional systems, by spatially separating the array of electrodes (which are used for contacting the electrogenic cells) from the corresponding analyzers. That is, in some embodiments, the array of electrodes are clustered in one area of the system's chip and the analyzers are clustered in a separate area of the chip. In this way, the electrode pitch can be significantly increased, thus allowing for the integration of a larger number of electrodes and analyzers. Furthermore, in this way, the space freed by spatially separating the electrodes from the amplifiers can be utilized to increase the size of the amplifiers, thus increasing the amplifiers' ability to provide large gains, and as a result, improving the immunity to noise.

The inventors have further appreciated that, due to the large impedance of electrogenic cells relative to the surrounding environment, obtaining signals from the cells that accurately represent the cell's activity is often challenging. Accordingly, the inventors have developed a method for improving the ability to electrically probe these cells which involves a reduction in the impedance of the cells. In some embodiments, a reduction in a cell's impedance may be achieved by generating a potential difference between the electrode used to probe the cell and a node positioned adjacent the cell. This potential difference may be generated, at least in some embodiments, by forcing an electric current to flow through the electrode. Once this potential difference is established, the difference in impedance between the cell and the surrounding environment may be reduced, thus facilitating electric probing of the cell.

The inventors have further appreciated that the ability to sense electrogenic activity can be substantially enhanced by using probing systems fabricated on integrated circuits (ICs) using complementary metal-oxide-semiconductor (CMOS) techniques. Compared to some conventional probing systems in which the various components that constitute the probing system are disposed on a common printed circuit board (PCB), but not on a common IC, the probing systems described herein allow for a substantial increase in the speed at which the electrogenic cells can be stimulated. Some conventional PCB-based probing system exhibit large delays (e.g., in the order of a few milliseconds) due to RC effects arising in the conductive traces. In some circumstances, these delays are greater than the duration of the action potentials being analyzed. The result is that the probing system exhibits a time resolution that is often too low to detect electrogenic activity. Being fabricated on a common IC, RC effects due to conductive traces are substantially diminished, thus reducing any delay introduced in the signals used for stimulating the electrogenic cells. As a result, the duration of the stimulus signals are not limited by the RC delays and can be controlled as desired. Certain electrogenic cells, for example, exhibit electrogenic activity for durations of less than 10 μs or even less than 1 μs. Probing systems of the types described herein provide sufficient time resolution to detect such short response signals.

The inventors have further recognized and appreciated that, in some circumstances, it may be desirable to enhance the biological connections existing among certain electrogenic cells, and/or inhibiting (or at least weakening) other biological connections. This may allow the behavior of certain biological connections to be isolated, thus allowing study of the electrogenic network of cells. The ability to enhance and/or inhibit biological connections, however, has some challenges. One challenge is due to the presence of electrogenic cells, and consequently of biological connections, in very large densities. Some studies have estimated that certain regions of the human brain contain up to 150 million neurons per square millimeter. As a result, large densities of analyzers are required to provide stimuli with suitable spatial resolutions. The inventors have appreciated that such large densities of analyzers may be achieved thanks to the use of ICs, which enable a substantial increase, over conventional systems, in the number of analyzers that can be integrated in a single probing system. To further improve the probing system's ability to study large densities of electrogenic cells, in some embodiments, nanowires may be used as electrodes for probing the cells. Compared to conventional electrodes, nanowires are sufficiently small to be able to probe single cells.

Some embodiments are directed to probing systems capable of forming arbitrary electrogenic networks, in which individual of groups of biological connections within the network can be arbitrarily strengthened and/or weakened. Strengthening of a biological connection may be achieved, at least in some embodiments, by stimulating the electrogenic cells at the ends of the biological connection with a timing consistent with their typical activation time. For example, neurons typically communicate with each other (using a combination of electrical and chemical signals), with signals (e.g., pulses) having durations in the tens to hundreds of microseconds. Thus, the biological connection between neurons may be strengthened by applying signals having durations in the same range, or may be weakened or inhibited by applying signals having durations outside this range.

As another example, cardiomyocytes typically communicate with each other with electrical signals (e.g., pulses) having durations in the tens of microseconds or less. Thus, the biological connection between cardiomyocytes may be strengthened by applying signals having durations in the same range, or may be weakened or inhibited by applying signals having durations outside this range.

Different cells may exhibit different activation times or intervals. Determining the duration of the activation intervals associated with the biological connections of a network and controlling the duration of the stimuli may be achieved using hardware disposed on an IC.

II. Electrogenic Analyzers

FIG. 1A is a schematic diagram illustrating an electrogenic network and a probing system. Probing system 100 may be implemented, in some embodiments, using electronic circuits such as complementary metal-oxide-semiconductor (CMOS) circuits. Electrogenic network 102 comprises a plurality of electrogenic cells $104_1$, $104_2$ ... $104_N$. These cells may be interconnected with one another in any suitable fashion and may communicate with one another via electric signals, such as action potentials. The cells of electrogenic network 102 may be probed used probing system 100 in vitro, in vivo, or in any other suitable way. These cells may be brain cells, heart cells, endocrine cells, or other types muscular cells. N may be between 1 and 10, between 1 and 100, between 1 and 1000, between 1 and 10000, between 1 and 100000, or greater than 100000.

Probing system 100 may comprise electrodes $106_1$, $106_2$ ... $106_N$, receivers $108_1$, $108_2$ ... $108_N$, stimulators $110_1$, $110_2$ ... $110_N$, detection cells $111_1$, $111_2$ ... $111_N$, and control read-out circuit 112. In some embodiments, these components of probing system 100 are integrated on a single integrated circuit. Of course, multiple integrated circuits may be used, as the application is not limited in this respect.

Electrodes $106_1, 106_2 \ldots 106_N$ may be placed in electrical contact with respective electrogenic cells. For example, the electrogenic cells may be placed in a container with an electrically conductive solution, and the electrodes may be placed in the solution. The electrodes may have areas ranging from 1 $nm^2$ to 1 $cm^2$, though other ranges are also possible.

Probing system 100 may be arranged in pixels, where each pixel comprises a stimulator and a receiver. Stimulators $110_1, 110_2 \ldots 110_N$ may be electrically connected to respective electrodes, and may be configured to stimulate respective electrogenic cells. In some embodiments, the stimulus may be provided as an electric current. In other embodiments, the stimulus may be provided as a voltage. Representative implementations for the stimulators are described in detail further below. When stimulated with an electric signal, an electrogenic cell may in response produce electric activity in conjunction with other cells of the network.

Receivers $108_1, 108_2 \ldots 108_N$ may be configured to monitor the electric activity of the respective cells. For example, the receivers may sense electric signals, such as voltages or currents, which may be representative of the cells' action potentials. In some embodiments, receivers $108_1, 108_2 \ldots 108_N$ comprise signal amplifiers (e.g., voltage amplifiers or trans-impedance amplifiers). In at least some of the embodiments in which stimulation of the cells is performed by providing electric currents (the current stimulation mode), the receivers may be configured to detect activity of the cells by sensing voltages. Contrarily, in at least some of the embodiments in which stimulation of the cells is performed by providing voltages (the voltage stimulation mode), the receivers may be configured to detect activity of the cells by sensing electric currents. The receiver and the corresponding simulator in a pixel are collectively referred to as an analyzer or cell analyzer. In some embodiments, the cell analyzer further includes digital circuitry (e.g., a processor) for interpreting the data captured by the receiver.

Detection cells $111_1, 111_2 \ldots 111_N$ may each include a sample and hold (S/H) circuit 114 ($114_1, 114_2 \ldots 114_N$ respectively) and a spike detector 116 ($116_1, 116_2 \ldots 116_N$ respectively). S/H circuit 114 may be configured to filter ripples generated by the respective stimulator that may inadvertently couple to the respective receiver. The presence of these ripples, in fact, may negatively affect the detection cell's ability to recognize signal spikes generated through electrogenic activity. The S/H circuits 114 may be arranged to filter ripples generated at the fundamental frequency of the stimulator.

Figure 17:
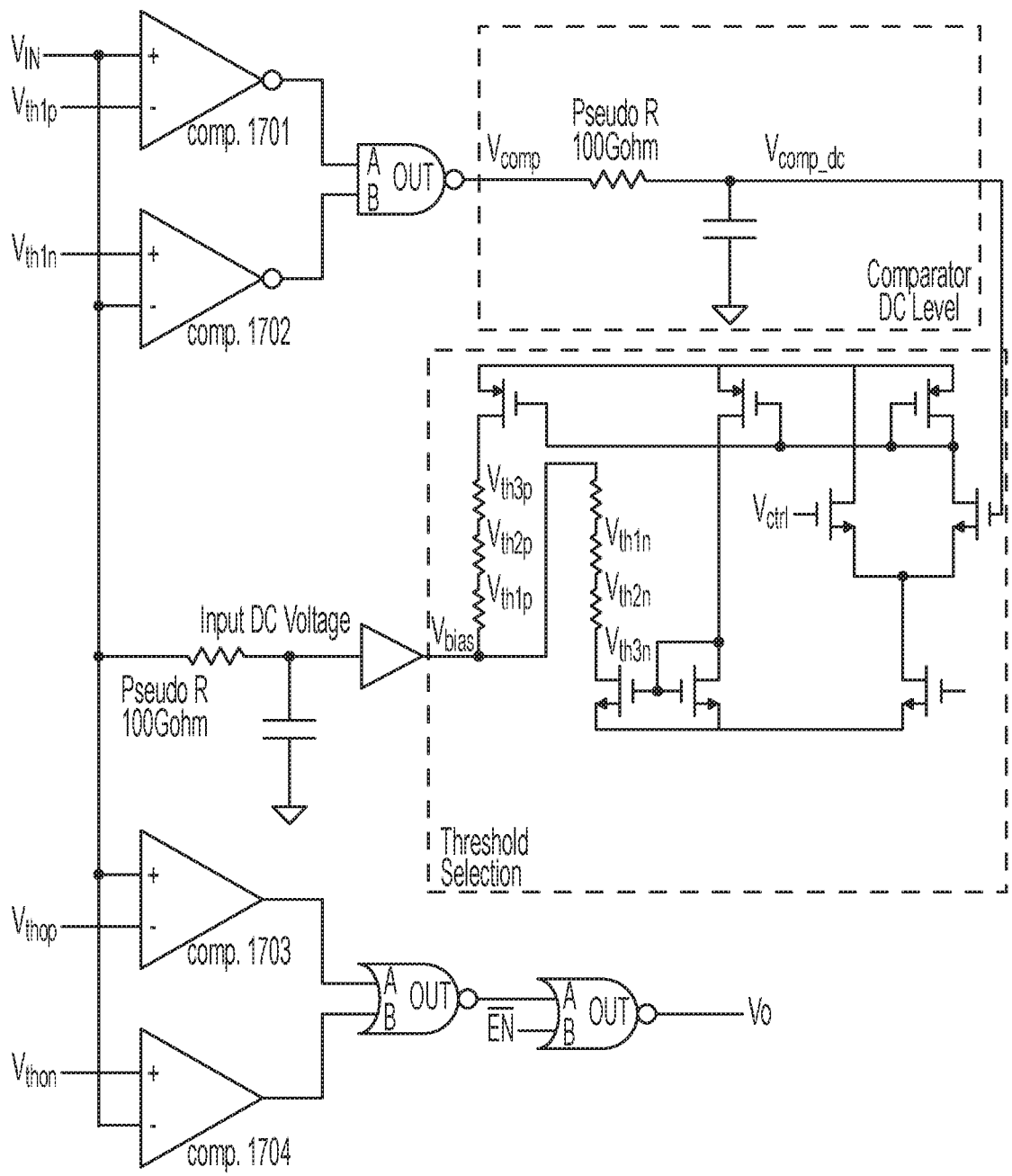
FIG. 17 is a circuit diagram illustrating a representative detection cell that may be used in connection with the probing system of FIG. 1A, according to some non-limiting embodiments.

Spike detectors 116 may be arranged to determine, based on the signal provided by the respective receiver, whether (and optionally the extent to which) electrogenic activity has occurred. In some embodiments, a spike detector 116 may include a memory, which may store therein reference data against which the measured signals may be compared to determine the nature of the response signals (e.g., to determine whether and/or the extent to which electrogenic activity has occurred). The reference data may be obtained in any of numerous ways, for example based on the noise level present in the spike detector. FIG. 17 illustrates an example of a circuit designed to generate such reference data, as will be described further below. The use of memories for storing reference values against which measured signals may be compared may facilitate the operations of the probing system without having to rely too heavily on software programs. In this way, the operations of the probing system may be ensured even if use of certain software program is precluded due to the use of ICs as the platform hosting the probing system.

The operations of a detection cell or portions of a detection cell may be activated or deactivated as desired. The ability to deactivate detection cells or portions thereof may be useful during the test phase, in which it is desirable to isolate different functions of the system. For example, in some circumstances, it may be desirable to test the functionality of a spike detector while at the same time bypassing the S/H circuit. Switches $S_{b1}$, $S_{b2}$ and $S_{b3}$ may be used to bypass the respective S/H circuits. In other circumstances, it may be desirable to test the functionality of a S/H circuit while deactivating the spike detector. Switches $S_{c1}$, $S_{c2}$ and $S_{c3}$ may be used to deactivate the respective spike detectors. In yet other circumstances, it may be desirable to test the functionality of probing system 100 while deactivating a detection cell. Switches $S_{a1}$, $S_{a2}$ and $S_{a3}$ may be used to deactivate the respective detection cells.

Probing system 100 may further include detection bus lines $130_1$, $130_2$ and $130_m$, and stimulation bus lines $132_1$, $132_2$ and $132_m$. These bus lines may be enabled or disabled depending on the state of the corresponding switch. As will be described in detail further below, enabling or disabling these bus lines may enable the formation of arbitrary electrogenic networks.

In some embodiments, probing system 100 may be fabricated such that receivers $108_1, 108_2 \ldots 108_N$, stimulator $110_1, 110_2 \ldots 110_N$, detection cells $111_1, 111_2 \ldots 111_N$, and control-readout circuit 112 are disposed on a common integrated circuit (IC). In this way, propagation delays of electrical signals passing throughout the system may be substantially reduced relative to non-integrated systems. Thus, short electrogenic activity (e.g., of less than 10 μs or less than 1 μs) may be sensed. Integrating these components on a common IC, however, has some challenges. One challenge stems from the fact that IC-based probing systems are not as easily programmable through software as PCB-based probing systems. PCB-based systems, in fact, often provide sufficient real estate to include connectors, controllers, and interfaces for enabling users to program the operations of their circuits utilizing software programs. By contrast, access to IC-based probing systems through software is more challenging, given their real estate limitations.

To obviate this limitation, some IC-based probing systems of the types described herein may be directly programmed via hardware. Specifically, some IC-based probing systems include hardware configured to determine whether (and optionally the extent to which) electrogenic activity has occurred based on the responses to the stimuli, and accordingly, to take further action based on this determination. In some embodiments the hardware may be programmed with a feedback loop arranged to determine the magnitude of the electrogenic response, and to adjust the magnitude or timing of the stimulus signals to increase or decrease the magnitude of the electrogenic activity as desired. For example, as will be described further below, some implementations may include memories that are hard coded with reference data.

Figure 2A:
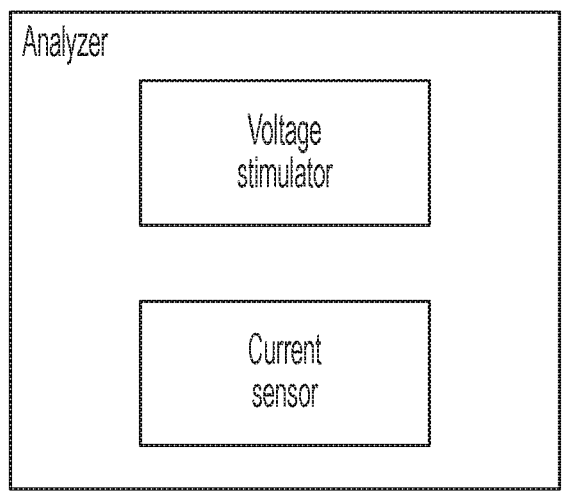
FIG. 2A is a block diagram of an analyzer configured to operate in a voltage stimulation mode, according to some non-limiting embodiments.
Figure 2B:
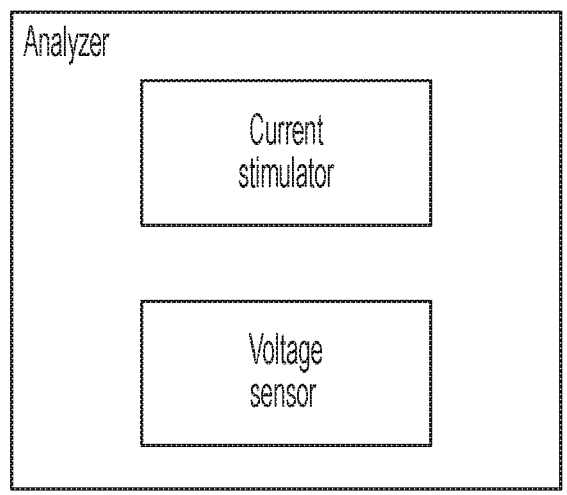
FIG. 2B is a block diagram of an analyzer configured to operate in a current stimulation mode, according to some non-limiting embodiments.

As will be described in detail further below, analyzers of the types described herein may be configured to operate in a voltage stimulation or in a current stimulation mode. In either arrangement, the analyzers may be configured to stimulate and sense electrogenic activity from the cells at the same time. Representative block diagrams illustrating respective analyzers for operating in the voltage stimulation mode and in the current stimulation mode are depicted in FIGS. 2A-2B. The analyzer of FIG. 2A includes a voltage stimulator and a current sensor. In some embodiments, the voltage stimulator and the current sensor share one or more circuit components, such as one common single-stage operational amplifier. The analyzer of FIG. 2B includes a current stimulator and a voltage sensor. In some embodiments, the current stimulator and the voltage sensor share one or more circuit components, such as one common single-stage operational amplifier. The inventors have appreciated that using a common single-stage amplifier, whether in the arrangement of FIG. 2A or FIG. 2B, may substantially decrease the analyzer footprint (i.e., the real estate occupied by the analyzer on the chip), which may allow for an increase in the density of pixels per unit area. Additionally, or alternatively, the analyzers may be arranged to allow for simultaneous stimulation of sensing of the cells. In some embodiments, this may achieved by including a common single-stage amplifier with negative feedback circuit, though not all embodiments are limited in this respect.

III. Strengthening and Weakening Biological Connections

Some embodiments are directed to probing systems capable of forming arbitrary electrogenic networks, in which individual or groups of biological connections of the network can be arbitrarily strengthened or weakened. As shown in FIG. 1A, not all electrogenic cells are connected to each other. For example, electrogenic cell $104_1$ and $104_N$ are not directly connected to each other. However, aspects of the present application enable the formation of arbitrary electrical connections between electrogenic cells, thus forming arbitrary electrogenic networks. Arbitrary electrogenic networks of the type described herein enable the activation of any cell of a network based on action potentials generated at any other cells of the network.

Figure 1B:
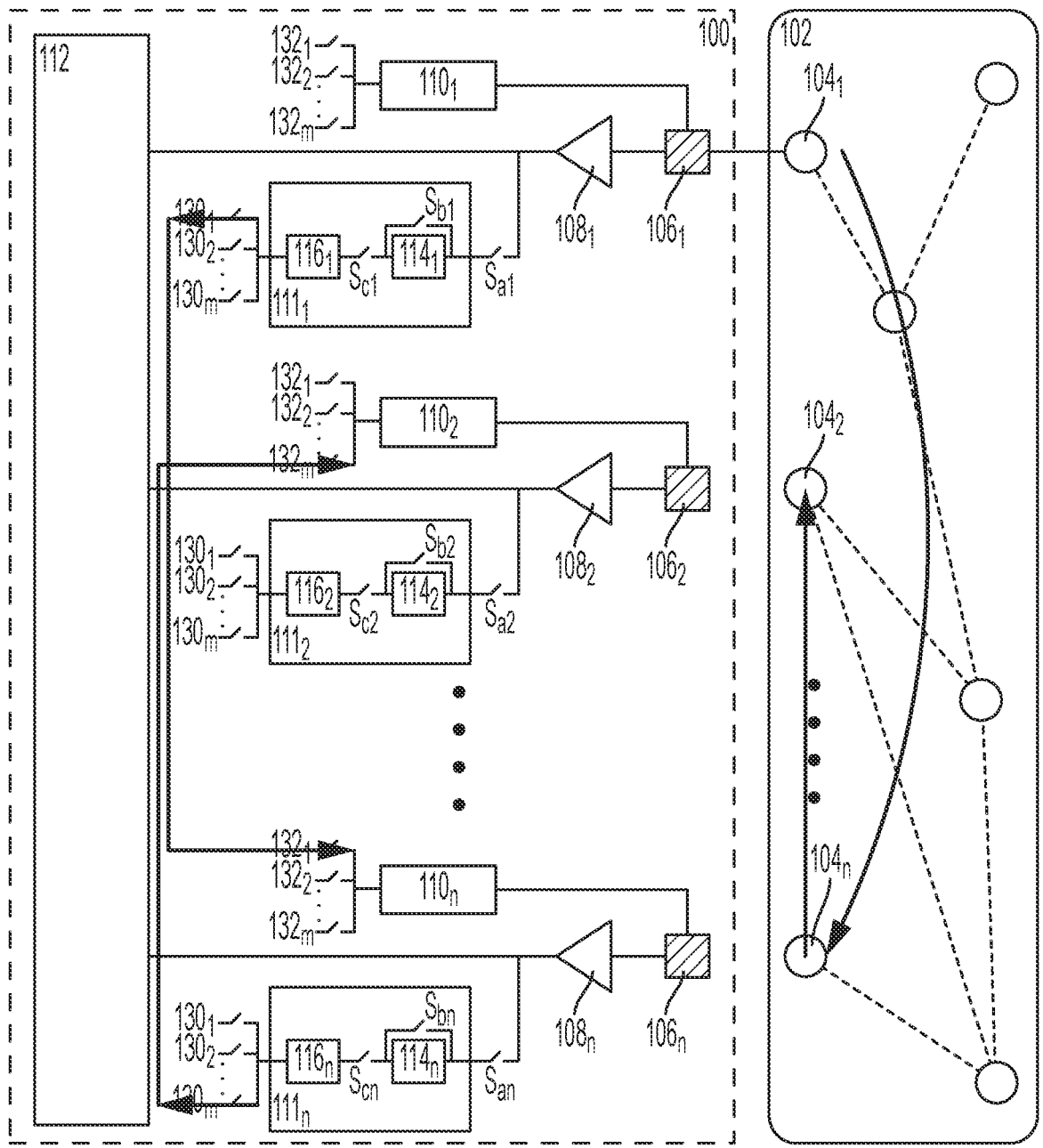
FIG. 1B is schematic diagram illustrating the electrogenic network and a probing system of FIG. 1A in which an arbitrary connection is formed, according to some non-limiting embodiments.

By way of illustration, electrogenic cell $104_1$ may be electrically connected to electrogenic cell $104_N$ using techniques of the type described herein. Electrogenic cell $104_1$ may be connected to electrogenic cell $104_N$ such that A) electrogenic activity at electrogenic cell $104_1$ triggers electrogenic activity at electrogenic cell $104_N$, and/or B) electrogenic activity at electrogenic cell $104_N$ triggers electrogenic activity at electrogenic cell $104_1$. FIG. 1B illustrates the probing system of FIG. 1A when programmed to connect electrogenic cell $104_1$ to electrogenic cell $104_N$. In some embodiments, function A) may be carried out by connecting detection cell $111_1$ to stimulator $110_N$. This connection may be achieved by enabling (using the corresponding switches) detection bus line $130_1$ and stimulation bus line $132_1$. In this way, action potentials occurring at electrogenic cell $104_1$ are detected at detection cell $111_1$, which in turn triggers stimulator $111_N$, which in turn stimulates electrogenic cell $104_N$. Similarly, function B) may be carried out by connecting detection cell $111_N$ to stimulator $110_1$. This connection may be achieved by enabling (using the corresponding switches) detection bus line $130_N$ and stimulation bus line $132_N$. In this way, action potentials occurring at electrogenic cell $104_N$ are detected at detection cell $111_N$, which in turn triggers stimulator $111_1$, which in turn stimulates electrogenic cell $104_1$.

Figure 1C:
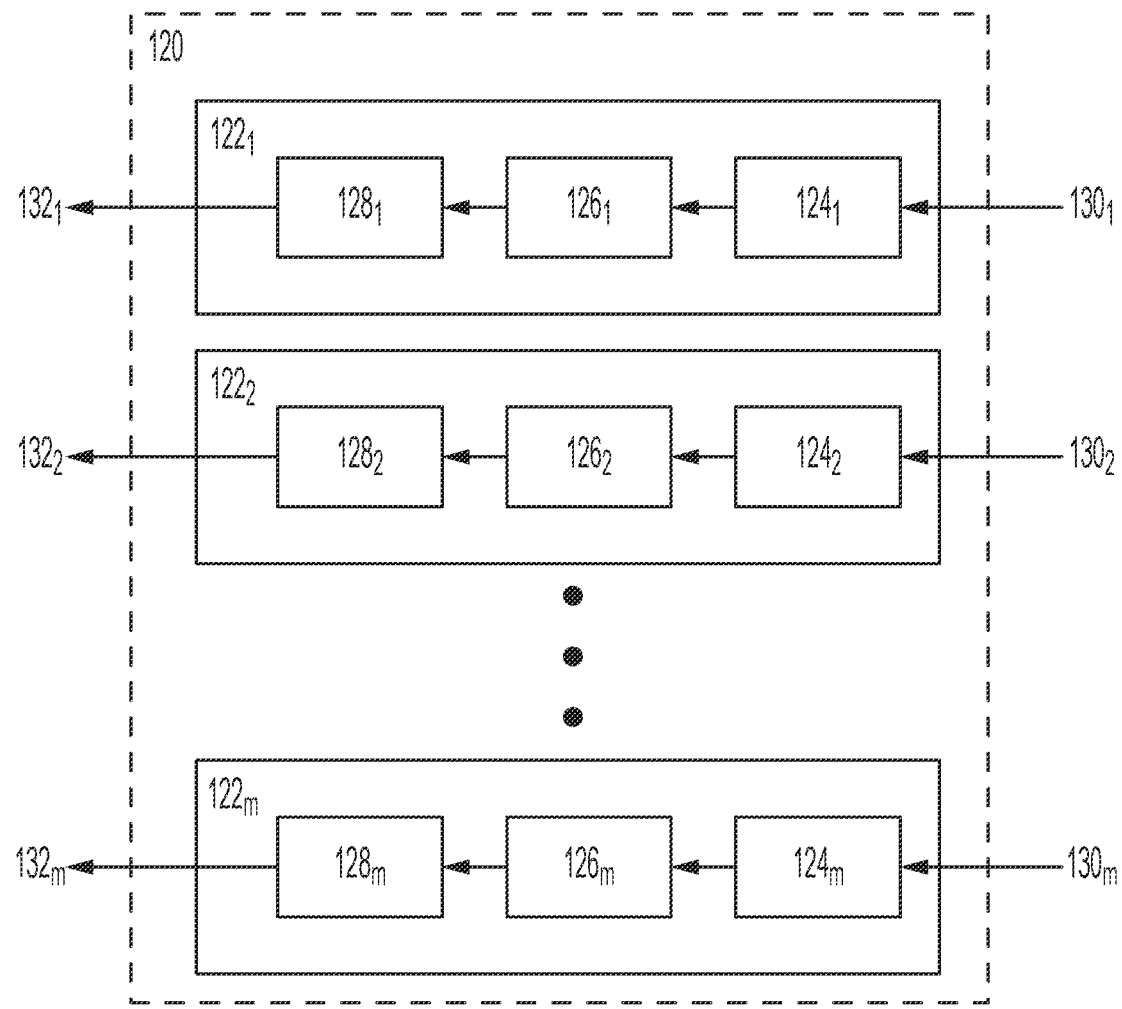
FIG. 1C is a schematic diagram illustrating a portion of the probing system of FIG. 1A in additional detail, according to some non-limiting embodiments.

The stimulation bus lines may be connected to the detection bus lines in any suitable way, one example of which is illustrated in FIG. 1C, in accordance with some embodiments. As shown, each detection bus line $130_1$, $130_2$ ... $130_m$ is connected to a respective stimulation bus line $132_1$, $132_2$ and $132_m$ via a stimulation trigger unit ($122_1$, $122_2$ and $122_m$). Stimulation trigger units $122_1$, $122_2$ and $122_m$ are collectively referred to herein as stimulation trigger array 120. Operations of a stimulation trigger unit may be enabled, in some embodiments, by closing the switches of the corresponding detection bus line and stimulation bus line. Each stimulation trigger unit may include a delay counter ($124_1$, $124_2$ and $124_m$, respectively), a pulse generator ($126_1$, $126_2$ and $126_m$, respectively), and a deadtime counter ($128_1$, $128_2$ and $128_m$, respectively). Of course, some of these components may be omitted in some embodiments. Additionally, or alternatively, other components not illustrated in FIG. 1C may be included in stimulation trigger array unit 120.

The delay counters may be configured to determine the delay with which an electrogenic cell responds relative to the occurrence of the stimulus signal that stimulates it and/or the duration of the pulse generated by an electrogenic cell. This information may be used, for example, to adjust the delay or the duration of the stimulus signals to strengthen or weaken a certain biological connection. For example, if it is determined that a biological connection responds with a certain delay and a certain duration, the biological connection may be strengthened if stimulated with a stimulus signal having substantially the same (e.g., within a 20% threshold) delay and/or duration. By contrast, the biological connection may be weakened if stimulated with a stimulus signal having a different delay and/or duration.

The pulse generators may be configured to generate pulses for driving the stimulators. Pulses generated using these pulse generators may have any suitable shape. The deadtime counters may be arranged to interrupt, for example for predefined periods of time, recording of electrogenic activity. Circuit 112 may include circuitry for controlling the state of the switches illustrated in FIG. 1A.

IV. Electrode Design

In some circumstances it may be desirable to reduce the impedance of the electrodes such that larger electric currents may be provided without having to significantly increase the voltage applied. In this way, the likelihood that bubbles are formed, for example via electrolysis of $H_2$ and $O_2$ molecules, is limited. The reduction of the likelihood of bubble formation may improve the integrity of the cell-electrode interface. In some cases, a reduction in the impedance of the electrode may advantageously lessen thermal noise, and a result, improve signal-to-noise-ratio.

Reduction of the electrodes impedance may be achieved, at least in some embodiments, by depositing a one or more materials having nanoscale roughness on the electrodes. Having a nanoscale roughness, these materials exhibit an effective surface that is substantially larger than the apparent surface that they occupy. As a result, the conductance (which is proportional to the surface's area) of the electrodes can be significantly increased. Examples of materials that may be deposited on the electrodes to decrease the impedance include, but are not limited to, platinum-black (Pt-black), iridium oxide (IrOx), gold flakes, carbon nanotubes, silver/silver chloride (Ag/AgCl), poly(3,4-ethylenedioxythiophene) (PEDOT)/poly(styrene sulfonate) (PSS), etc.

Figure 3A:
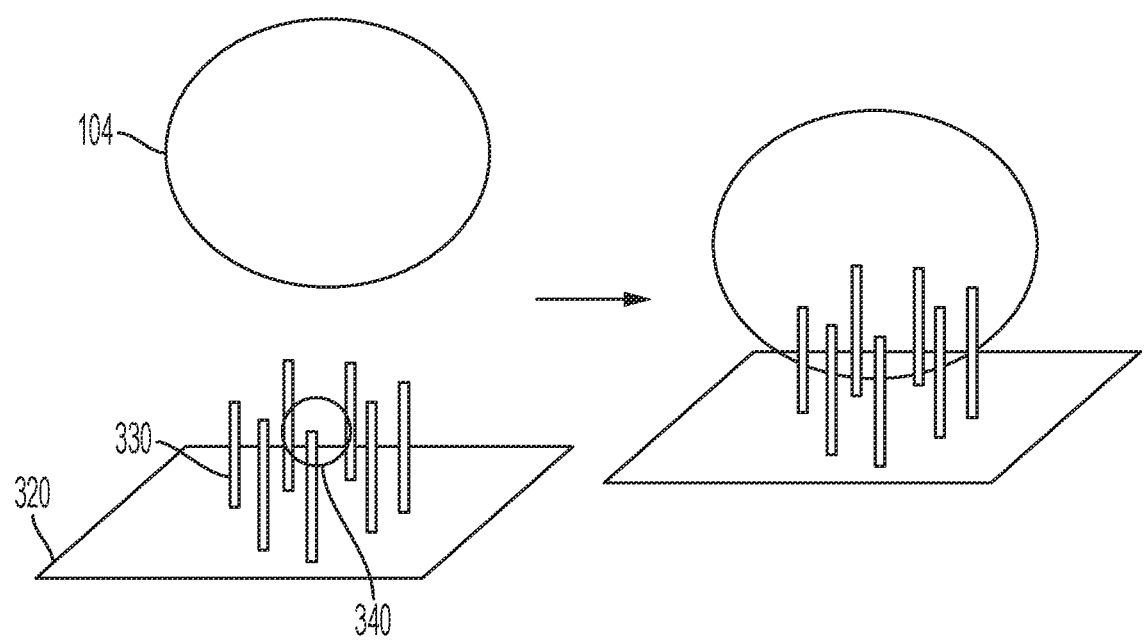
FIG. 3A is a schematic diagram illustrating an array of nanowires before and after insertion into a cell, according to some non-limiting embodiments.

The electrodes may have any suitable shape. In some embodiments, the electrodes $106_1$, $106_2$ ... $106_N$ may be shaped as nanowires or as pluralities of nanowires. One example of an electrode being shaped as a plurality of nanowires is depicted in FIG. 3A, where a cell 104 is brought into contact with a substrate 320 having an array of vertical nanowires 330. The substrate may be planar or substantially planar in some embodiments. One or more of the ends 340 of nanowires 330 may be inserted into cell 104. As discussed herein, some or all of the nanowires may be individually addressable, e.g., for recording and/or for applying an electrical force to the cell. Nanowires that may be used can be formed of material with low cytotoxicity, such as silicon, silicon oxide, silicon nitride, silicon carbide, iron oxide, aluminum oxide, iridium oxide, tungsten, stainless steel, silver, platinum, and gold. Other suitable materials include aluminum, copper, molybdenum, tantalum, titanium, nickel, tungsten, chromium, or palladium. In some embodiments, the nanowire comprises or consists essentially of a semiconductor. Typically, a semiconductor is an element having semiconductive or semi-metallic properties (i.e., between metallic and non-metallic properties). An example of a semiconductor is silicon. Other non-limiting examples include elemental semiconductors, such as gallium, germanium, diamond (carbon), tin, selenium, tellurium, boron, or phosphorous. In other embodiments, more than one element may be present in the nanowires as the semiconductor, for example, gallium arsenide, gallium nitride, indium phosphide, cadmium selenide, etc.

Figure 3B:
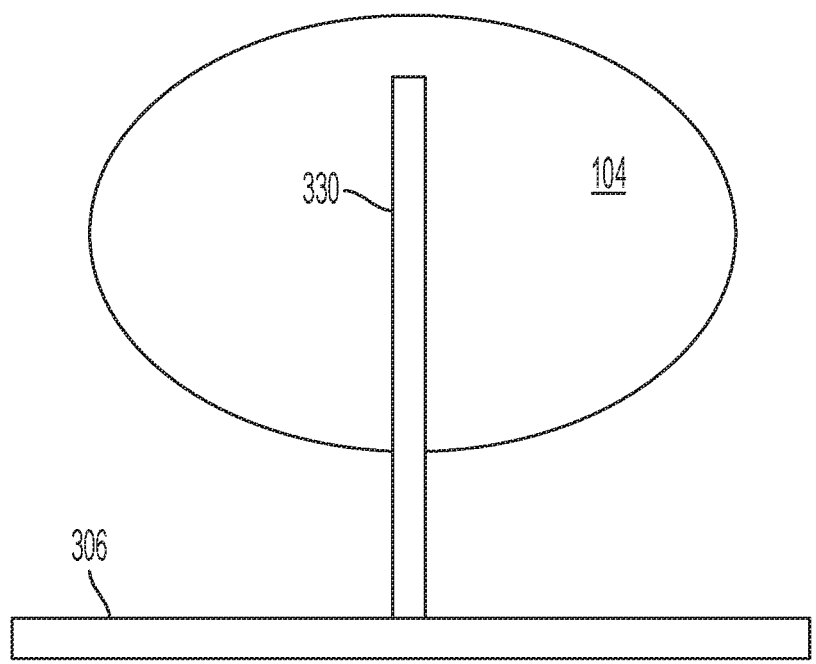
FIG. 3B is a schematic diagram illustrating a nanowire connected to a metal pad and inserted into a cell, according to some non-limiting embodiments.
Figure 3C:
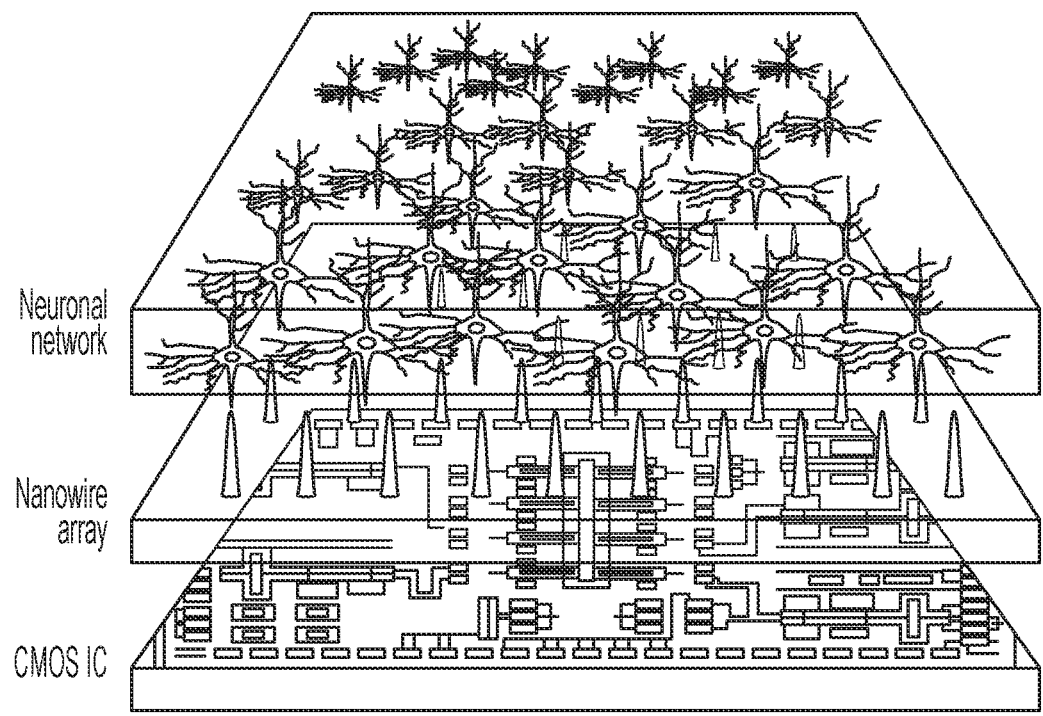
FIG. 3C is a schematic diagram illustrating a representative system for probing a neuronal network comprising a complementary metal-oxide-semiconductor (CMOS) integrated circuit (IC) and a nanowire array, according to some non-limiting embodiments.

The nanowires may be upstanding or substantially oriented vertically, with respect to the surface in some embodiments. For example, on average, the upstanding nanowires may form an angle with respect to a substrate of between about 80° and about 100°, between about 85° and about 95°, or between about 88° and about 92°. In some cases, the average angle is about 90°. Examples of such nanowires may be found in, for example, Int. Pat. Appl. Pub. No. WO 2016/112315, published Jul. 14, 2016, incorporated herein by reference in its entirety. As used herein, the term "nanowire" (or "NW") refers to a material in the shape of a wire or rod having a diameter in the range of 1 nm to 1 micrometer (µm). FIG. 3B illustrates a representative nanowire 330 that is positioned in contact with an metal pad 306 and a cell 104. The metal pad may be in communication with a corresponding receiver and a stimulator. As further illustrated in FIG. 3C, arrays of nanowires may be used to probe multiple cells. Stimulation and monitoring activity may be performed using CMOS circuits. While FIG. 3C illustrates a nanowire array for probing a neuronal network, nanowires of the types described herein can be used to probe any type of electrogenic cell network.

In some embodiments, the nanowires may be fabricated using photolithographic or electron beam (e-beam) techniques. FIGS. 4A-4F illustrate a processing sequence for fabricating nanowires, according to some non-limiting embodiments. As illustrated in FIG. 4A, a layer of dielectric material 404 (e.g., SiO₂) is deposited or epitaxially grown on a substrate 402 (e.g., a silicon substrate). In some embodiments, the dielectric layer may be grown using plasma-enhanced chemical vapor deposition (PECVD). However, it should be appreciated that other dielectric deposition techniques (such as physical vapor deposition) may be used. The dielectric layer 404 may have any suitable thickness, such as between 100 nm and 10 µm, between 100 nm and 8 µm, between 100 nm and 6 µm, between 100 nm and 4 µm, between 100 nm and 2 µm, between 100 nm and 1 µm, between 100 nm and 500 nm, between 500 nm and 10 µm, between 500 nm and 8 µm, between 500 nm and 6 µm, between 500 nm and 4 µm, between 500 nm and 2 µm, between 500 nm and 1 µm, between 1 µm and 10 µm, between 1 µm and 8 µm, between 1 µm and 6 µm, between 1 µm and 4 µm, between 1 µm and 2 µm, between 2 µm and 4 µm, between 2.5 µm and 3.5 µm, or within any suitable range within such ranges. Other ranges are also possible.

In the processing step depicted in FIG. 4B, a photoresist mask 406 may be deposited on the dielectric layer 404, and lithography or e-beam may be used to etch portions of the dielectric layer. In some embodiments, anisotropic etching is used (e.g., dry etching) to form elongated shapes. As illustrated, a plurality of dielectric pillars 408 may result from the etching process. The pillars may have any suitable thickness (e.g., diameter, in the embodiments in which the pillars have cylindrical shapes). The thickness of the pillars may be between 100 nm and 10 µm, between 100 nm and 5 µm, between 100 nm and 2 µm, between 100 nm and 1 µm, between 100 nm and 800 nm, between 100 nm and 700 nm, between 100 nm and 600 nm, between 100 nm and 500 nm, between 100 nm and 400 nm, between 100 nm and 300 nm, between 200 nm and 800 nm, between 200 nm and 600 nm, between 400 nm and 800 nm, between 400 nm and 600 nm, or within any suitable range within such ranges. Other ranges are also possible.

Optionally, in the processing step of FIG. 4C, a further etching process may be performed to thin the pillars 408. For example, the pillars may be thinned to a thickness (e.g., diameter) that is between 10 nm and 1 µm, between 10 nm and 800 nm, between 10 nm and 800 nm, between 10 nm and 600 nm, between 10 nm and 400 nm, between 10 nm and 500 nm, between 10 nm and 400 nm, between 10 nm and 300 nm, between 10 nm and 200 nm, between 10 nm and 100 nm, between 10 nm and 50 nm, between 50 nm and 800 nm, between 50 nm and 500 nm, between 50 nm and 400 nm, between 50 nm and 300 nm, between 50 nm and 200 nm, between 50 nm and 150 nm, between 50 nm and 100 nm, between 75 nm and 500 nm, between 75 nm and 500 nm, between 75 nm and 400 nm, between 75 nm and 300 nm, between 75 nm and 200 nm, between 75 nm and 150 nm, between 75 nm and 125 nm, between 75 nm and 100 nm, or within any suitable range within such ranges. Other ranges are also possible. Thinning of the pillars may be accomplished using wet etching techniques, in some embodiments.

In the processing step of FIG. 4D, the pillars 408 may be covered with a metal layer 410 (e.g., one or more of gold, platinum, copper, aluminum, silver, palladium, etc.). In some embodiments, metal layer 410 may be covered with dielectric layer 412 (e.g., SiO₂ and/or Al₂O₃). The dielectric layer may be formed via atomic layer deposition (ALD). In the processing step of FIG. 4E, a layer of photoresist 414 may be deposited to at least partially cover the pillars. In the processing step of FIG. 4F, etching may be performed to remove the portion of the dielectric layer 412 that is not covered by photoresist. Subsequently, removal of the photoresist layer may be performed. The resulting structure may have a tip that is conductive (being covered with metal layer 410) and may be used as a nanowire. Materials having a nanoscale roughness, such as platinum-black (Pt-black), iridium oxide (IrOx), gold flakes, carbon nanotubes, silver/silver chloride (Ag/AgCl), poly(3,4-ethylenedioxythiophene) (PEDOT)/poly(styrene sulfonate) (PSS), etc. may be deposited on the nanowires to decrease impedance.

The electrodes may also have other shapes as well. In some embodiments, the electrodes may be formed to have conical shapes (e.g., pipette shapes). Conical shapes may be useful, for example, for additional strength, and/or to facilitate entry of the electrodes into cells, e.g., at the apex of the cone. Conical shapes may be created on a surface, for example, using positive or negative lithographic techniques, such as photolithography. A material having nanoscale roughness such as platinum black may be deposited inside the cone to reduce impedance, e.g., using deposition techniques such as electrodeposition.

Figure 5C:
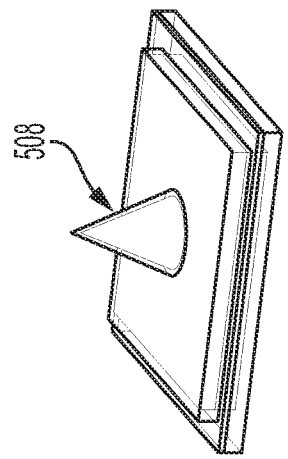
FIGS. 5A-5F collectively illustrate a representative process for fabricating a conical electrode, according to some non-limiting embodiments.
Figure 5F:
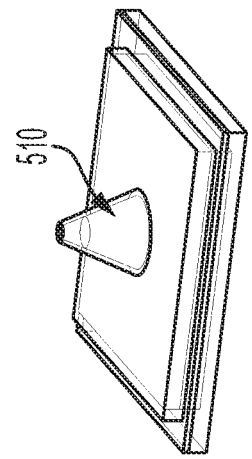
Figure 5B:
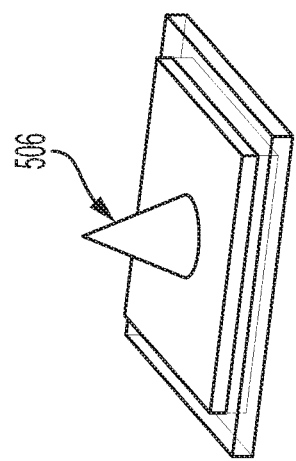
Figure 5E:
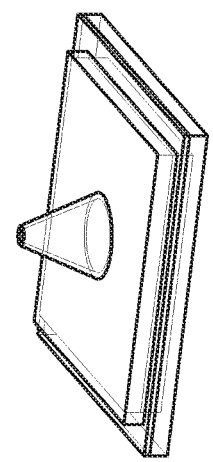
Figure 5A:
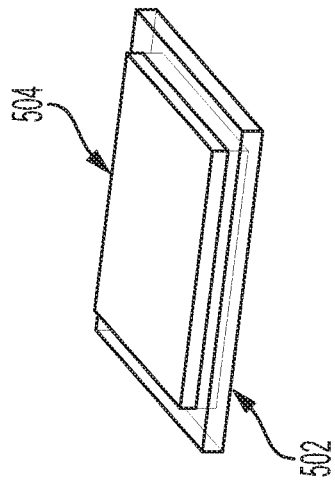
Figure 5D:
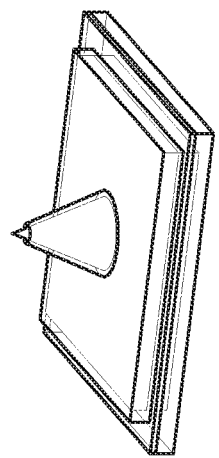

An example representative process flow for forming conically shaped electrodes is illustrated in FIGS. 5A-5F. In the process step of FIG. 5A, a metal pad 504 is formed on substrate 502. Subsequently, a sacrificial cone 506 made of photoresist may be formed on the metal pad (FIG. 5B) and may be encapsulated by a dielectric layer 508 (FIG. 5C), which may be formed via ALD. The conical structure may be patterned by scanning a laser diode with its optical defocus configured such that small mask features are resolved within a depth of focus that is smaller than the resist thickness. After forming the conical oxide shell, an opening in the upper portion of the dielectric encapsulating layer may be formed (FIG. 5D), the photoresist sacrificial cone may be removed (FIG. 5E) and Pt-black and/or other nanoscale surface rough materials such as those described herein can be electrodeposited inside the conical dielectric shell, e.g., to achieve a desired electrode impedance (FIG. 5F). This may allow the patterning of 3D microstructures with a single photolithography step and then electrodepositing of a low-impedance electrode.

In yet another set of embodiments, the electrodes may be arranged as cavities. Cavity electrodes may be useful for reducing impedance while having less signal leakage, e.g., from a cell such as a neuron. In some cases, cavity electrodes may be useful for addressing single cells. In some cases, a cavity may include a relatively large enclosed chamber, sealed except for a relatively small opening on one wall of the chamber. The opening may be used to address cells or other targets. The chamber may have any suitable 3-dimensional shape, e.g., cubical, block, pyramidal, tetrahedral, spherical, cylindrical, etc. Such chambers may be created, for example, using positive or negative lithographic techniques, such as photolithography. A conductive material such as platinum black may be deposited on some or all of the inner surface of the chamber, e.g., using deposition techniques such as electrodeposition.

Figure 6D:
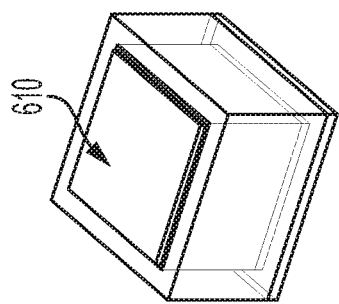
FIGS. 6A-6H collectively illustrate a representative process for fabricating an electrode shaped as a cavity, according to some non-limiting embodiments.
Figure 6H:
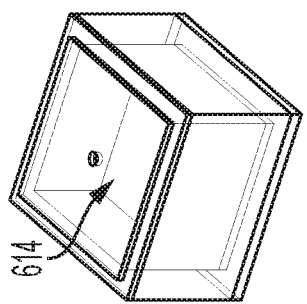
Figure 6C:
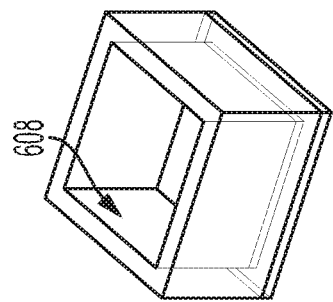
Figure 6G:
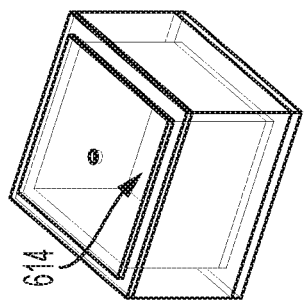
Figure 6B:
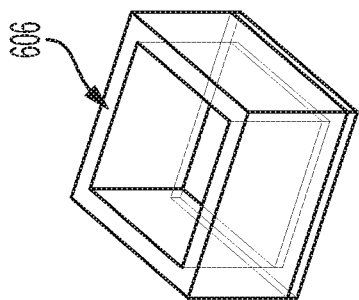
Figure 6F:
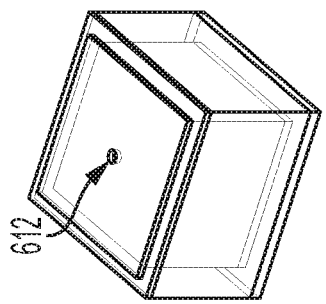
Figure 6A:
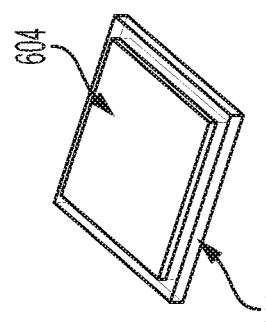
Figure 6E:
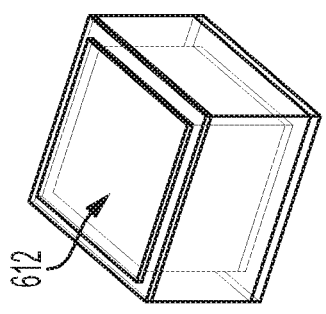

An example representative process flow for forming cavity electrodes is illustrated in FIGS. 6A-6H. In the process step of FIG. 6A, a metal pad 604 is formed on substrate 602. Subsequently, a well may be formed by depositing and dry etching dielectric material into walls 606 (FIG. 6B). In the step of FIG. 6C, the inner walls of the well may be coated with a metal layer 608 (e.g., gold, platinum, copper, aluminum, silver, palladium). Subsequently, a photoresist 610 may be used to fill up the well (FIG. 6D). As shown in FIG. 6E, the top surface of the well may be covered with a dielectric layer 612 (e.g., $SiO_2$ or $Al_2O_3$), for example using ALD. In the processing step of FIG. 6F, a hole 612 may be formed through the dielectric layer (and optionally through the underlying photoresist) using a dry etching process. As shown in FIG. 6G, the photoresist filling the well may be dissolved through hole 612, thus creating an enclosed cavity 614. Additional deposition of nanomaterials—including but not limited to platinum-black (Pt-black), iridium oxide (IrOx), gold flakes, carbon nanotubes, silver/silver chloride (Ag/AgCl), poly(3,4-ethylenedioxythiophene) (PEDOT)/poly(styrene sulfonate) (PSS)), etc.—can be used to reduce the electrode impedance even further (FIGS. 6G-6H). The large surface area of the electrode obtained within the cavity in this manner may exhibit a low impedance. The small pore that interfaces with neurons may limit the signal leakage.

Figure 7A:
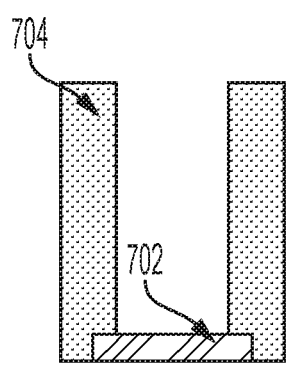
FIGS. 7A-7B collectively illustrate a representative process for fabricating an electrode shaped as a tube, according to some non-limiting embodiments.
Figure 7B:

As yet another example, electrodes may be formed with tube or cylindrical shapes, as shown in FIGS. 7A-7B. Such electrodes may be created, for example, using positive or negative lithographic techniques, such as photolithography. In some cases, a conductive material such as platinum black may be deposited on some or all of the inner surface of the tube, e.g., using deposition techniques such as electrodeposition.

In the process step of the example of FIG. 7A, a tube may be formed having a metal pad 702 as a base and dielectric or photoresist 704 as walls. As shown in FIG. 7B, a metal (e.g., e.g., gold, platinum, copper, aluminum, silver, palladium, platinum-black (Pt-black), iridium oxide (IrOx), gold flakes, carbon nanotubes, silver/silver chloride (Ag/AgCl), poly(3,4-ethylenedioxythiophene) (PEDOT)/poly(styrene sulfonate) (PSS), etc.) may be deposited on inside that tube to cover the base and the inner walls.

In one aspect, the electrodes may be contained within a plurality of wells, e.g., containing cells. In some cases, the cells may be studied in parallel fashion, e.g., to test a variety of drugs or potential drug candidates, to study the effect of one or more compositions or agents on one or more cells or cell types, or the like. For example, in some cases, the wells may be arranged as in multiwell plates, which may be of any size.

However, in certain embodiments, the wells are arranged as in the dimensions of a microwell plate, e.g., having standard dimensions (about 5 inches×about 3.33 inches, or about 128 mm×86 mm) and/or standard numbers of wells therein. For example, there may be 6, 24, 48, 96, 384, 1536 or 3456 wells present. In some cases, the device may include multiwell plates, which may be fabricated from any suitable material, e.g., polystyrene, polypropylene, polycarbonate, cyclo-olefins, or the like. Microwell plates can be made by injection molding, casting, machining, laser cutting, or vacuum sheet forming one or more resins, and can be made from transparent or opaque materials. Many such microwell plates are commercially available.

V. Cells

Devices such as those described herein may be used with any suitable type of cell. For example, the cell may be a prokaryotic cell or a eukaryotic cell. The cell may be from a single-celled organism or a multi-celled organism. In some cases, the cell is genetically engineered, e.g., the cell may be a chimeric cell. The cell may be bacteria, fungi, a plant cell, an animal cell, etc. The cell may be from a human or a non-human animal or mammal (e.g., mouse, rat, pig, etc.). For instance, if the cell is from an animal, the cell may be a cardiac cell, a neural cell (e.g., a cortical neuron, an olfactory receptor neuron, an olfactory sensory neuron, etc.), an osteocyte, an osteoblast, a muscle cell (e.g., a cardiomyocyte), etc. The cell may be a primary cell or an immortalized cell. In some cases, the cell is a primary mammalian neuron (e.g., human cortical neuron, rat cortical neuron, etc.).

In addition, it should be noted that in some embodiments, the cells may be cultured on the substrate using any suitable cell culturing technique, e.g., before or after insertion of electrodes. For example, mammalian cells may be cultured at 37° C. under appropriate relative humidities in the presence of appropriate cell media.

In yet another aspect, cells, such as neurons, are positioned in electrical communication with one or more electrodes, e.g., as discussed herein. The electrodes may be used to stimulate the cells, and/or determine an electrical condition of the cells. More than one electrodes may be positioned in electrical communication with the cell, for example, in distinct regions of the cell. In some cases, the electrodes may be positioned such that they are relatively close together, for example, spaced apart by no more than about 200 nm. The electrodes wires may be disposed on a substrate, and the cells may be adhered or plated onto the substrate, for example, using cell adhesion factors such as polylysine.

In one aspect of the invention, cells such as neurons are positioned in electrical communication with one or more electrodes, as described herein. Any cell can be used which exhibits electrical behavior, such as membrane potential. For instance, the cell may be a cell in which it is desired to measure the membrane potential (e.g., instantaneously, as a function of time, in response to an external stimulus, such as a drug or an applied external electrical potential, etc.), the cell may be a cell which can be used to detect electric fields (for example, cells from the ampullae of Lorenzini, which is present in certain types of organisms such as sharks), or the cell may be a cell that can produce an electrical signal, for example, a neuron (which is able to produce an action potential), a cardiomyocyte, or an electrocyte (which is used in organisms such as electric eels or electric ray to produce an electrical discharge). In some cases, a neuron comprises one or more ion channels (e.g., a voltage-gated ion channel, a ligand-gated ion channel). In certain cases, the ligand-gated ion channel of a neuron is a cholinergic receptor (e.g., a protein that responds to the binding of acetylcholine). The cholinergic receptor may, in some cases, belong to the family of neuronal nicotinic acetylcholine receptors (nAchRs). Neuronal nicotinic acetylcholine receptors, which are typically pentameric complexes comprising different combinations of alpha (e.g., $\alpha 2$-$\alpha 10$) and beta (e.g., $\beta 3$, $\beta 4$, $\beta 5$) subunits, may be a potential drug target for neurological disorders such as Parkinson's disease, Alzheimer's, and/or hyperactivity disorders.

The electrode may be in electrical communication with a portion of the cell, i.e., the electrode may be positioned, relative to the cell, such that the electrode is able to determine or affect the electrical behavior of the cell, and/or of a region of the cell. The electrodes may be of dimensions such that the electrode can be used to measure or determine a distinct region of a cell. As a non-limiting example, if the cell is a neuron, the electrode may be positioned such that the electrode is able to determine or affect the electrical behavior of a portion of the axon, dendrite, and/or soma of the neuron. The electrode may be in physical contact with the cell, or not in physical contact but positioned such that changes in the electrical state of the cell are able to affect the electrical state of the electrode, and/or vice versa. In some embodiments, at least a portion of the electrode is inserted in the cell. One or more than one electrode may be in electrical communication with the cell.

In one set of embodiments, a cell in electrical communication with an electrode can be electrically stimulated by passing a current or applying a potential to the electrode, which may be used to affect the electrical state of the cell. For example, the membrane potential of a cell may be altered upon electrical stimulation, or a neuron can be stimulated to cause the neuron to polarize (e.g., hyperpolarize) or depolarize upon the application of sufficient current or potential. In some cases, a current or potential may be applied to the electrode by a stimulator unit. Additionally, in some cases, the electrical state of the cell can be determined using a sensing electrode, such as another electrode, as discussed herein.

In another set of embodiments, a change in an electrical state of a cell, such as cell polarization or depolarization, an action potential, a change in plasma membrane potential (e.g., a postsynaptic potential), or the like may cause a change in the electrical state of an electrode in electrical communication with the cell, such as a change in conductance, which change can be determined and/or recorded in some fashion, e.g., using techniques known to those of ordinary skill in the art. In some cases, the change in electrical state (e.g., an electrical signal) may be stored (e.g., in digital memory), output to a display, and/or modified/converted in some manner. Accordingly, one embodiment of the invention provides for the determination of an electrical state of a cell using an electrode. According to some embodiments, at least a portion of the electrode is inserted in the cell (e.g., in the intracellular space). In some cases, an electrical signal may be transmitted from the cell to the electrode, and the signal may subsequently be transmitted to an amplifier unit in electrical communication with the electrode. In some cases, the cell may also be one which was electrically stimulated, e.g., electrically stimulated by applying current or a potential to an electrode, such as another electrode, that is in electrical communication with the cell. As a specific example, the electrical state of a neuron, or a portion thereof (e.g., an axon, a dendrite, a soma, etc.) may be determined using a nanoscale wire in electrical communication with the neuron; for instance, the neuron may depolarize (e.g., due to exposure to a chemical species, or to a nanoscale wire or other electrode able to cause the neuron to depolarize), causing the formation and propagation of an action potential through the neuron, which action potential may be determined using an electrode. In this way, one or more than one neuron may be studied. In some embodiments, electrical signals from one or more neurons forming an interconnected network may be recorded using one or more electrodes. Accordingly, the characteristics of an interconnected network (e.g., a neuronal network) may be investigated.

In some embodiments, the electrical state of the cell may be altered by exposing the cell to a chemical species suspected of being able to alter the electrical state of the cell. For example, a chemical species able to facilitate the depolarization of a cell, or a chemical species that inhibit the depolarization of a cell, can be used to alter the electrical state of the cell, and in some cases, to cause a cell such as a neuron to polarize (e.g., hyperpolarize) or depolarize. In one set of embodiments, the chemical species comprises drugs or drug candidates, neurotoxins, neurotransmitters, or the like, which may be suspected of being able to treat or alter the behavior of the cells. In some cases, the drugs or drug candidates may target one or more types of ion channels. As a non-limiting example, the drugs or drug candidates may target neuronal nicotinic acetylcholine receptors (nAchRs).

Due to their small size, more than one electrode may be positioned in electrical communication with the cell, or portion thereof, according to another set of embodiments. For example, at least 3, at least 4, at least 5, at least 10, at least 15, at least 20, at least 25, at least 30, at least 35, at least 40, at least 45, or at least 50 or more electrodes may be positioned in electrical communication with the cell, or with a portion thereof, e.g., axons and/or dendrites if the cell is neuron. In some embodiments, more than one electrode may be inserted in the cell, or portion thereof. For example, at least 3, at least 4, at least 5, at least 10, at least 15, at least 20, at least 25, at least 30, at least 35, at least 40, at least 45, or at least 50 or more electrodes may be inserted in the cell, or with a portion thereof. Thus, a plurality of electrodes may each be used in some embodiments to independently measure a distinct region of the cell. If more than one nanoscale wire is present, the electrodes may each independently be the same or different. Non-limiting examples of electrodes include any of those described herein.

VI. Monitoring of Electrogenic Activity

As described above, electrogenic cells stimulators may be employed to stimulate cells to produce electrogenic activity. FIG. 8 illustrates a non-limiting implementation of an electrogenic stimulator used in electrogenic monitoring. As illustrated, electrode 106 is coupled to receiver 108 and stimulator 110 (which may be implemented according to any of the embodiments described above and below), and to cell 104. Cell 104 may be placed in a container 150, which may comprises for example an electrolyte. In the embodiments in which the container includes an electrolyte, the impedance of the electrolyte may be substantially lower than the impedance of the cell 104. As a result, electrically probing of the cell using receiver 108 may be challenging, since the majority of the signal received would solely (or for the most part) depend on the impedance of the electrolyte, rather than the impedance of the cell.

In some embodiments, the impedance of the cell at location "B" (inside the cell), may be decreased by generating a voltage between electrode 106 and a location "A" (outside the cell). This voltage may be generated for example by forcing a current sourced by stimulator 110 to flow through electrode 106. When such a current is flown, the impedance at location A is decreased. As a result, the impedance at location B relative to the surrounding electrolyte is also decreased, thus facilitating the monitoring of the cell's electrogenic activity.

In some embodiments, current may be sourced by the stimulator for the duration of a monitoring session, which may range between one second and several hours.

Figure 8A:
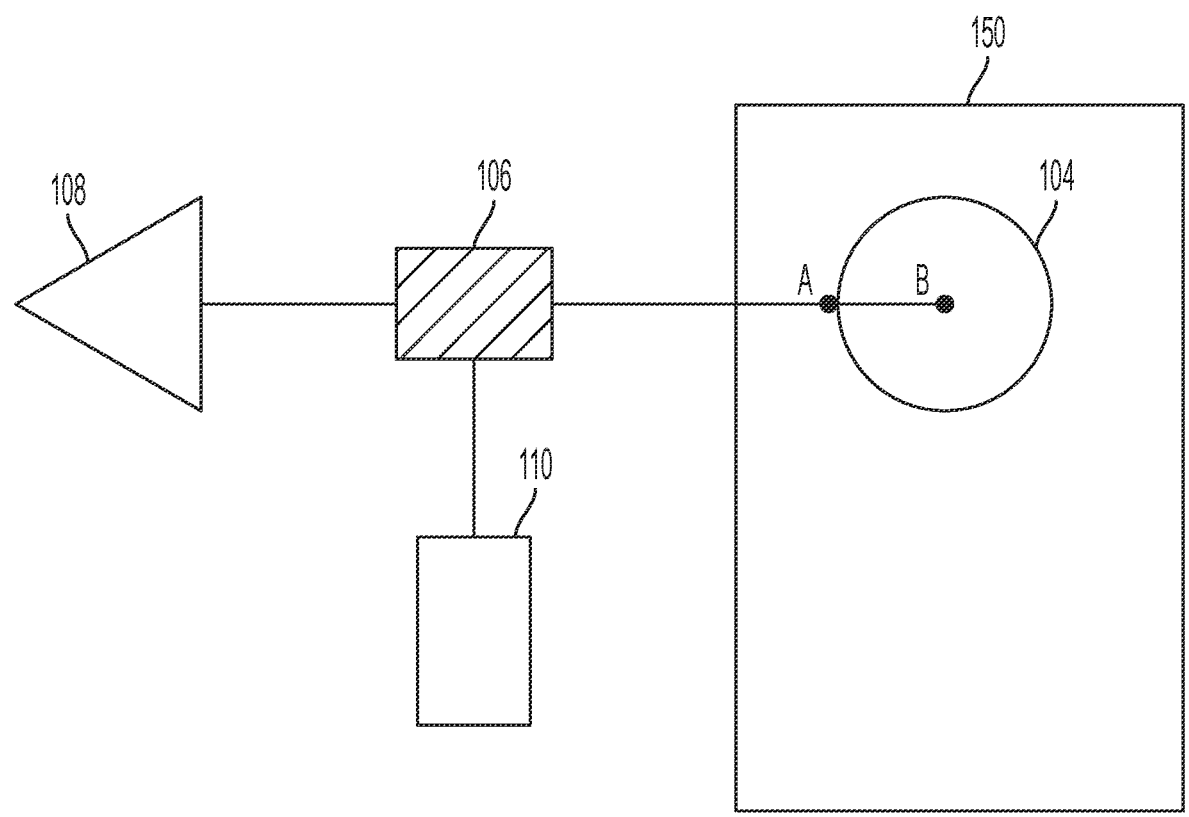
FIG. 8A-8E collectively illustrate a representative system for monitoring electrogenic activity, according to some non-limiting embodiments.
Figure 8B:
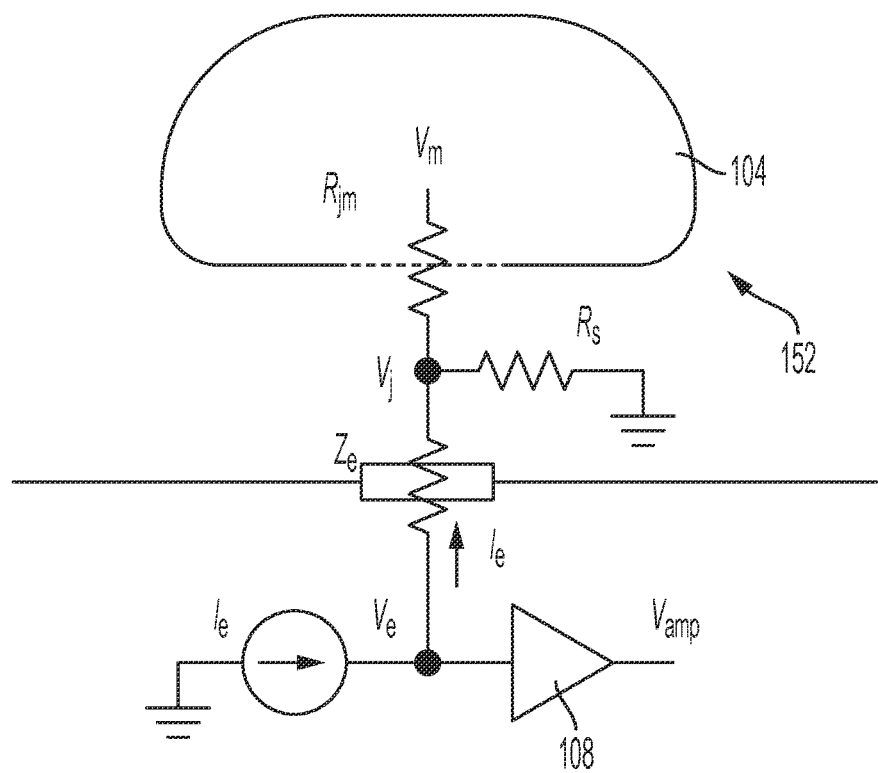

FIG. 8B is a circuit diagram illustrating a system for monitoring electrogenic activity, according to some embodiments. As shown, a cell 104 is immersed in an electrolyte 152, which may be contained inside container 150 of FIG. 8A. The cell exhibits an input resistance Rjm, which may be for example more than 106 GΩ or more than 100 GΩ. Voltage Vm (the quantity to be sensed) may represent for example an action potential.

Electrode 106 is represented in FIG. 8B by its impedance Ze. The electrode is coupled to receiver 108. Rs represents the resistance of the electrolyte, which may be for example between 1 MΩ and 100 MΩ. Since Rjm is, at least in some embodiments, a few orders of magnitude greater than Rs, attempts to sense to sense Vm using receiver 108 will result in the sensing of Vj, rather than Vm. The inventors have appreciated, however, that sensing of Vm may be enabled by injecting (or extracting) a current through the electrode into the electrolyte, which results in a substantial decrease in the value of Rjm. Accordingly, stimulator 110 includes a current generator Ie configured to drive a current through the electrolyte.

Figure 8C:
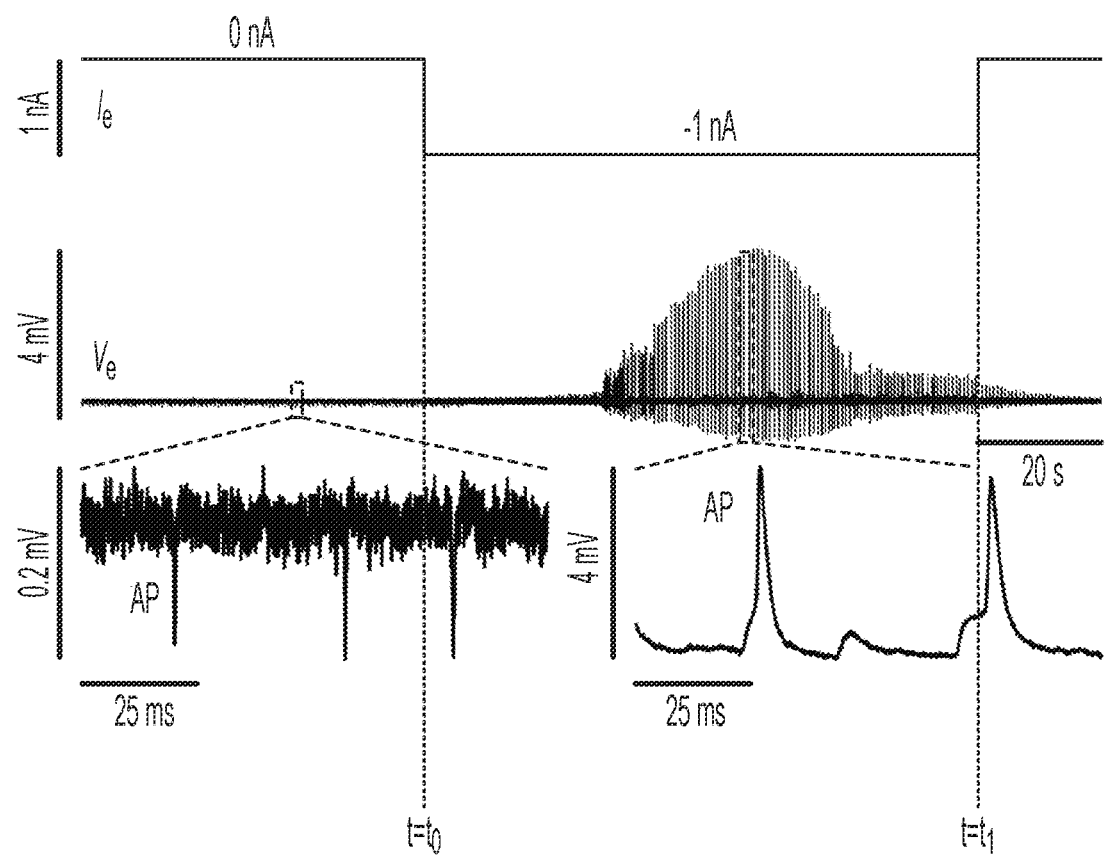

FIG. 8C is a plot illustrating the response of the system when a current is generated with the current generator of FIG. 8B. Specifically, FIG. 8C illustrates an example of a current Ie, and the response of the system in terms of voltage Ve, at the electrode 106. Prior to t=t0, no current is generated (0 nA). In this period of time, voltage Ve exhibits an amplitude of the order of 0.2 mV. Voltage peaks of about 0.1 mV in amplitude are observed. Given their low amplitude, these peaks are an attenuated and distorted representation of the intracellular activity (e.g., action potentials).

At t=t0, the current Ie output by the current generator is set to −1 nA (where the negative sign indicates a current flowing away from the electrolyte). It should be appreciated that most of the current generated flows through electrode 106, rather than receiver 108, since receiver 108 exhibits a capacitive input impedance, at least in some embodiments. After t0, but prior to t1, Ve exhibits several peaks with amplitude of the order of 4 mV. These peaks are the result of electrogenic activity in the cell. As illustrated, the amplitude of the peaks is significantly higher than the noise floor, thus making it easily detectable by receiver 108. The increase in the peaks of Ve is due to a reduction in Rjm when Ie is set to −1 nA. Further sub-threshold signals are able measured with the increased signal-to-noise ratio, in this example excitatory post synaptic potentials, which are unable to be resolved from the noise without the application of Ie=−1 nA. Of course, other values of Ie other than −1 nA are also possible in other embodiments.

Figure 8D:
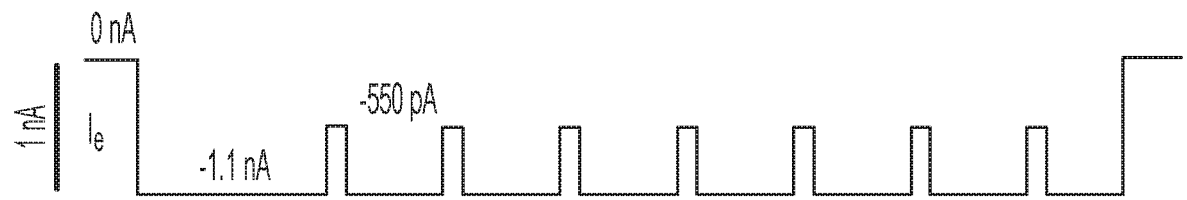
Figure 8E:
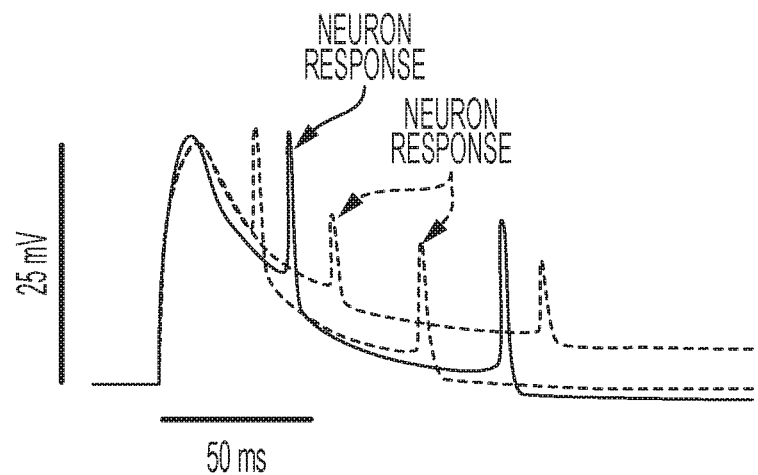

In some embodiments, to further enhance the cell's response, the stimulators may generate a first current value for reducing the value of Rjm, and subsequently a second current value for stimulating electrogenic activity. In some embodiments, the stimulator may alternate between the first and second current values, for example in a periodic fashion. An example of a current Ie that may be generated to reduce resistance Rjm and stimulate electrogenic activity is illustrated in the plot of FIG. 8D, in accordance with some embodiments. In this case, a −1.1 nA current is used to reduce Rjm, and a −550 pA is used to stimulate electrogenic activity. In response to such a current, voltage Ve responds with the behavior of FIG. 8E. As shown, multiple peaks are generated in response to the −550 pA pulses. The peaks are the result of electrogenic activity within different cells. The peaks have amplitude of the order of 20 mV, thus significantly greater than those of FIG. 8C. It should be noted that voltage Ve exhibits a decaying exponential characteristic owing to the fact that the electrode behaves with a low-pass response. The decaying exponential may be eliminated (or at least reduced) using a high-pass filter.

VII. Design of the Electrogenic Analyzers

As described above, electrogenic analyzers of the types described herein may be configured to stimulate the cells and sense their responses in overlapping phases (e.g., simultaneously). This may be accomplished, at least in some embodiments, by using different physical quantities for the stimulus and the response signal. For example, some embodiments use a voltage stimulation mode, in which the stimulus is provided as a voltage and the response is sensed as an electric current. By contrast, other embodiments use a current stimulation mode, in which the stimulus is provided as a current and the response is sensed as a voltage.

Figure 9A:
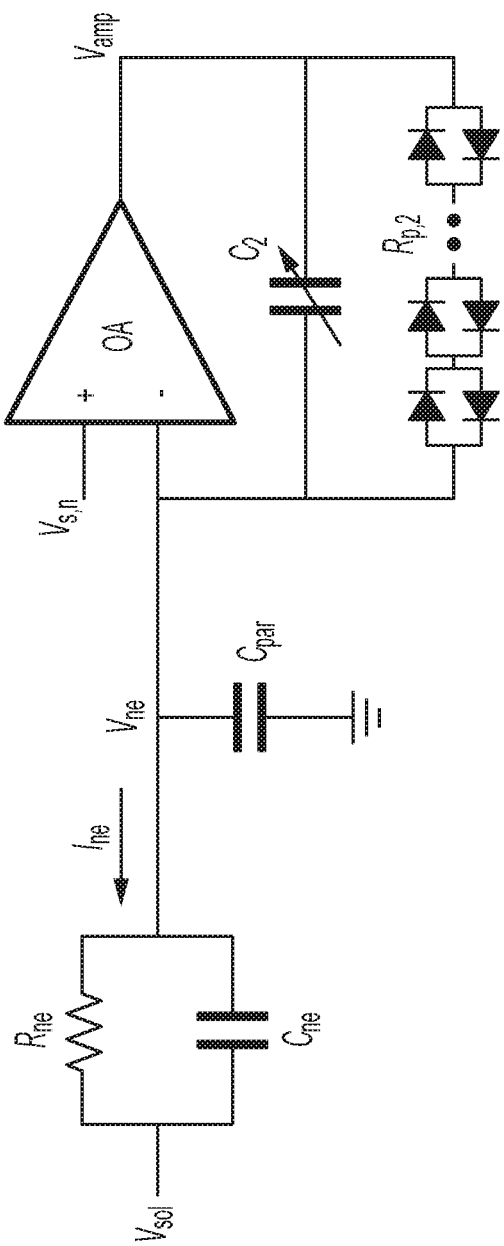
FIG. 9A-9C illustrate examples of analyzers configured to operate in a voltage stimulation mode, according to some non-limiting embodiments.

A representative cell analyzer configured to operate in the voltage stimulation mode is illustrated in FIG. 9A. In the illustrated circuit diagram, resistor $R_{ne}$ and capacitor $C_{ne}$ model the impedance of an electrode 106, $C_{par}$ represents the circuits parasitic capacitance, the device labelled "OA" represents an operational amplifier, $C_2$ is a capacitor having an adjustable capacitance, and $R_{p,2}$ is a bank of antiparallel diodes connected in series. Capacitor $C_2$ and diodes $R_{p,2}$ may collectively form a negative feedback loop between the inverting input terminal and the output terminal of the operational amplifier. In some embodiments, the diodes of $R_{p,2}$ may be switchable (may be turned on and off), thus allowing for variations of the resistance of the feedback loop.

Stimulation of the cells may triggered by the application of a voltage $V_{s,n}$ at one of the input terminals of the operational amplifier (e.g., the non-inverting input terminal). When $V_{s,n}$ is applied to the operational amplifier, the negative feedback loop allows an electric current to pass through it, which in turn causes the voltage $V_{ne}$ to follow $V_{s,n}$. The delay with which $V_{ne}$ follows $V_{s,n}$ may depend on the capacitance of $C_2$ and/or the number of active diodes. The voltage $V_{ne}$ may be applied to the electrode, which in turn may stimulate an electrogenic cell with a voltage $V_{sol}$.

Detection of the electrogenic activity may be performed by sensing the electric current $I_{ne}$ generated by the cells. It should be appreciated that the current $I_{ne}$ may be directed towards the cells or away from them. In some embodiments, detection of the current may be enabled by the presence of the feedback loop. That is, when $I_{ne}$ flows through the operational amplifier's feedback loop, a voltage $V_{amp}$ is generated in response. Overlapping stimulation and detection of the cells may be enabled, at least in some embodiments, by the fact that the stimulation signal path and the sensing signal path pass through the same feedback loop of the operational amplifier OA. Accordingly, the diodes may be arranged in an antiparallel configuration so as to allow currents to flow in both directions (e.g., one direction for the stimulation and the opposite direction for the response).

According to one aspect of the present disclosure, diodes are used in the feedback loop rather than conventional resistors to provide a sufficiently large impedance to enable detection of weak currents. For example, in cases in which it is expected that the current generated by the cells is 1 nA or less, the resistance of the diodes may be set to 1 GΩ or more, and in cases in which it is expected that the current generated by the cells is 100 pA or less, the resistance of the diodes may be set to 10 GΩ or more.

Figure 9C:
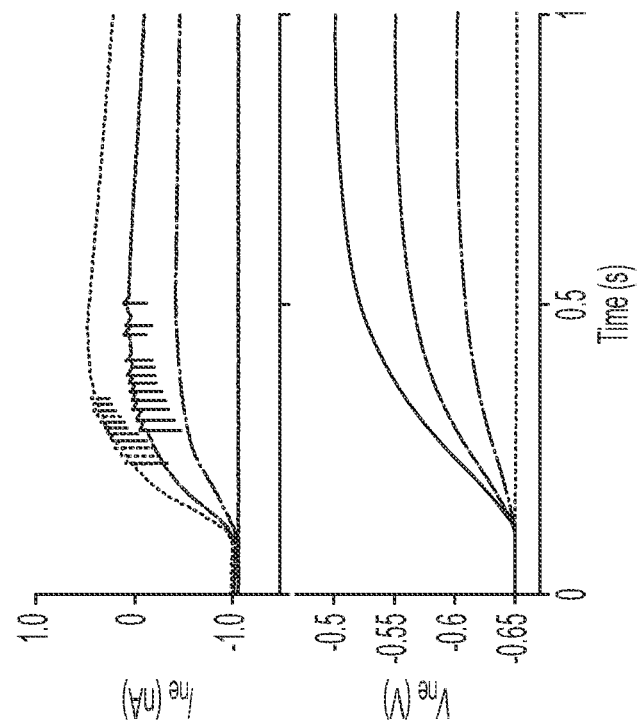
Figure 9B:
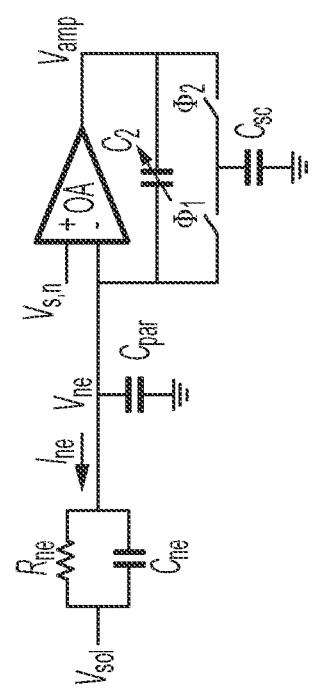

Another representative cell analyzer configured to operate in the voltage stimulation mode is illustrated in FIG. 9B. In the illustrated circuit diagram, switches ϕ1 and ϕ2 and capacitor Csc are included in the feedback of the OA and serve as a switched capacitor. Non-overlapping clock phases, ϕ1 and ϕ2, may prevent shoot through from the output, Vamp, to the negative terminal of the op-amp. The reference voltage Vs,n may set the potential of the electrode, Vne, while the electrode current, Ine, is measured.

The recorded output voltage, Vamp, can be expressed as Vamp=Vs,n+Ine/(fsc×Csc), where fsc is the switching frequency of the switched capacitor Csc, with non-overlapping clock phases ϕ1 and ϕ2. To limit high frequency signals and to ensure amplifier stability, capacitor C2 may be included in the feedback to set the bandwidth of the current measurement to fsc·Csc/(2π×C2). In one example, Csc is set to 40 fF and fsc to 35 kHz. The result is an effective feedback switched capacitance resistance of [1/(fsc×Csc)]=700 MΩ. Capacitor C2 may be for example between 25 fF and 100 fF for measurement bandwidths of ~9 kHz and ~2 kHz, respectively.

Intracellular recording can be performed using the illustrated configuration by applying a negative electrode voltage with respect to the potential set by a reference electrode. In some experiments, voltages of −0.6 V to −0.7 V were effective at gaining intracellular access. No spontaneous neuron activities were observed due to the low impedance of the electrode clamping the neuron's membrane potential. In some embodiments, stimulation of an electrogenic cell can be performed by varying over time the voltage applied to the electrode, as shown in the experiment of FIG. 9C, which involved the stimulation of a rat's neuron. The short spikes observed in the current represent neuron responses to the voltage stimulation.

Figure 10:
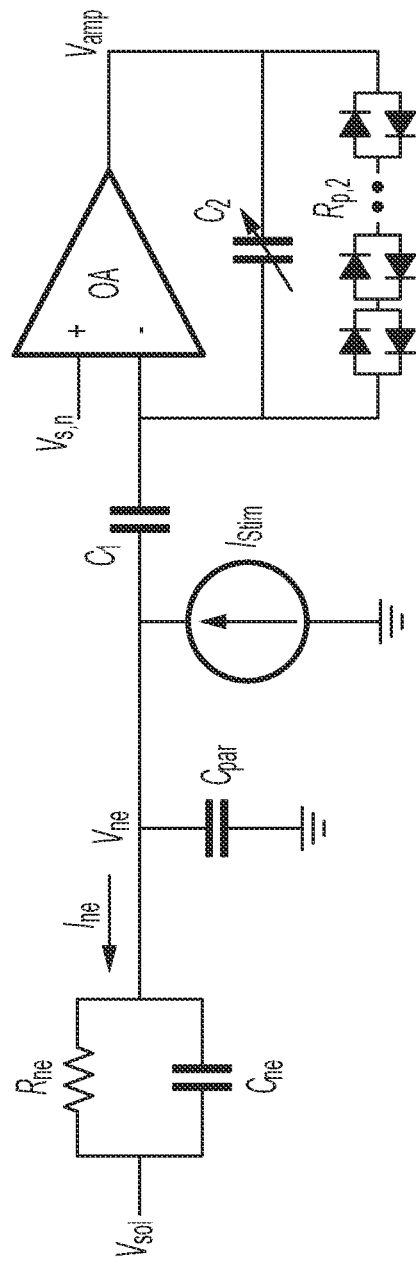
FIG. 10 is a circuit diagram illustrating a representative analyzer configured to operate in a current stimulation mode, according to some non-limiting embodiments.

A representative cell analyzer configured to operate in the current stimulation mode is illustrated in FIG. 10. In the illustrated circuit diagram, resistor $R_{ne}$ and capacitor $C_{ne}$ model the impedance of an electrode 106, $C_{par}$ represents the circuits parasitic capacitance, the device labelled "OA" represents an operational amplifier, $C_2$ is a capacitor having an adjustable capacitance, and $R_{p,2}$ is a bank of antiparallel diodes. Capacitor C2 and diodes $R_{p,2}$ may collectively form a negative feedback loop between the inverting input terminal and the output terminal of the operational amplifier. Current generator $I_{stim}$ may be used to stimulate the cells. In some embodiments, the diodes of $R_{p,2}$ may be switchable thus allowing for variations of the resistance of the feedback loop.

Stimulation of the cells may be performed using current generator $I_{stim}$. In some embodiments, a capacitor $C_1$ is positioned between the current generator and the operational amplifier. The presence of the capacitor may be used to isolate the operational amplifier from the current generator, thus ensuring that the majority of the stimulus current flows to the cells. In this way, the stimulus signal and the response signal are decoupled from each other, thus allowing for overlapping stimulation and detection. Detection of the electrogenic activity may be performed by sensing the electrode's voltage $V_{ne}$. Accordingly, the feedback loop is arranged such that the output voltage $V_{amp}$ tracks voltage $V_{ne}$. The resistance of $R_{p,2}$ may be chosen to provide amplify $V_{ne}$. In some embodiments, the resistance of $R_{p,2}$ is set to a value that is greater than 100 GΩ, thus allowing for the detection of voltages that are less than 10 pV. In some embodiments, the resistance of $R_{p,2}$ is set to a value that is greater than 1 TΩ, thus allowing for the detection of voltages that are less than 1 pV.

It should be appreciated that in some embodiments, as illustrated in FIGS. 9-10, a single operational amplifier may be used for the stimulation and sensing of electrogenic activity. Compared to conventional systems that utilize more than one operational amplifiers for a stimulator and/or for a receiver, this analyzer may occupy significantly less real estate on the chip, such allowing for increases in the overall size of the array. The footprint reduction may allow for an increase in the size of capacitor $C_1$, which may lead to improvements in the signal-to-noise ratio. In some embodiments, however, using a single amplifier may lead to an increase in the power consumed to maintain a desired gain-bandwidth product.

VIII. Detection Cell

An example of a detection cell that may be used as detection cell 116 is illustrated in FIG. 17, in accordance with some non-limiting embodiments. The detection cell illustrated is configured to detect spikes (e.g., action potentials) from noise by adjusting a threshold based on the background noise level. In particular, the threshold may be set to be sufficiently above the noise level to reduce the likelihood of false alarms, but sufficiently low to detect weaker spikes. The signal generated by receiver $108_1$ is input to the detection cell at input port Vin. Background noise is provided as input to ports Vth1p and Vth1n. Together with the circuits labeled "comparator DC level" and "threshold selection," comparators 1701 and 1702 are configured to determine the standard deviation σ of the background noise. A multiple of the standard deviation σ, for example, 3σ or 5σ, is provided an input voltage at input ports Vthop and Vthon. The multiple of the standard deviation serves as the threshold to determine whether a spike has occurred. Comparators 1703 and 1704 are used to compare, in a differential fashion, the multiple of the standard deviation with the input signal. If the input signal exceeds the threshold, the detection cell determines that a spike has occurred.

IX. Chip Layout

The inventors have recognized and appreciated that the analyzer's ability to sense electrogenic activity may be enhanced by integrating a large number of pixels (e.g., at least 4096 pixels) in the same chip. In this way, the activity of a large number of cells may be monitored at the same time, thus producing an improved indication of the activity of the overall network. The inventors have further recognized that the number of pixels may be increased by decreasing the pitch of the electrode array. In some embodiments, the pitch of the electrode arrays may be decreased by spatially separating, on the chip, the array of receivers and stimulators from the array of electrodes. In this way, the separation between adjacent electrodes is not affected by the fact that the receivers and stimulators occupy significantly more real estate that the electrodes. The electrode array pitch may be less than 40 µm, less than 30 µm, less than 20 µm or less than 10 µm.

In one example, technology nodes as small as 0.18 µm or less may be used for the analyzers described herein. Using such small technology nodes may provide a number of benefits. Non-limiting examples of such benefits include: 1) reduction of the footprint, and/or 2) ability to integrate the capacitors above the transistors, thus freeing up space to increase the size of the transistors, which in turn may improve the signal-to-noise ratio. Using such small technology nodes, however, may have one or more drawbacks. One drawback is the reduction in the voltage that can be used to power the circuits without damaging the circuits.

Figure 11:
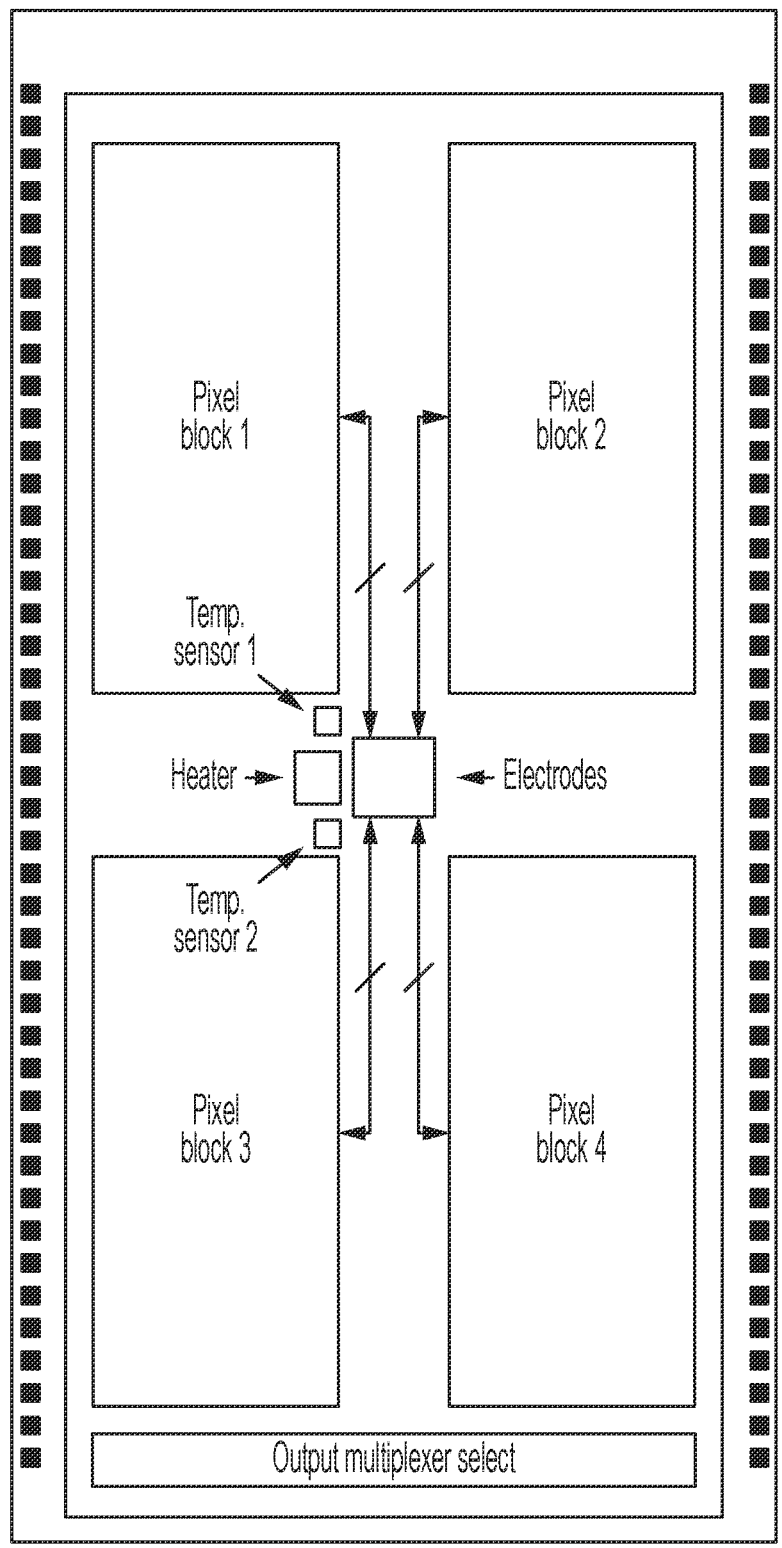
FIG. 11 is a schematic diagram illustrating a representative chip layout for the analyzers described herein, according to some non-limiting embodiments.

A representative chip layout is illustrated in FIG. 11. As illustrated, the array of electrodes (labelled "electrodes") is spatially separated from the array of receivers and stimulators (the pixel blocks of FIG. 11). In this way, the overall size of the electrode array may be decoupled from the size of the receivers and stimulators, thus allowing for a significant increase in the number of electrogenic cells that can be monitored. In one example, the electrode pitch is 20 µm, though the pitch may be reduced even further.

A possible drawback caused by the separation between the electrodes and the circuits is the increased parasitic capacitance (due to the metal trace between the circuits and the electrodes). To reduce the likelihood that the this extra capacitance causes coupling between adjacent electrodes/pixels, in some embodiments the pixel-to-electrode wire traces may be surrounded by ground shields. In one example, the total parasitic capacitance due to the electrode trace in the presence of ground shields may be ~1-2 pF (depending upon the length of the trace). In most biological experiments, this parasitic capacitance is sufficiently low to not affect the outcome of experiments.

In some embodiments, heaters and temperature sensors (as shown in FIG. 11) may be included in the chip to allow precise temperature control of the temperature of the cells.

X. Experimental Results

Figure 12:
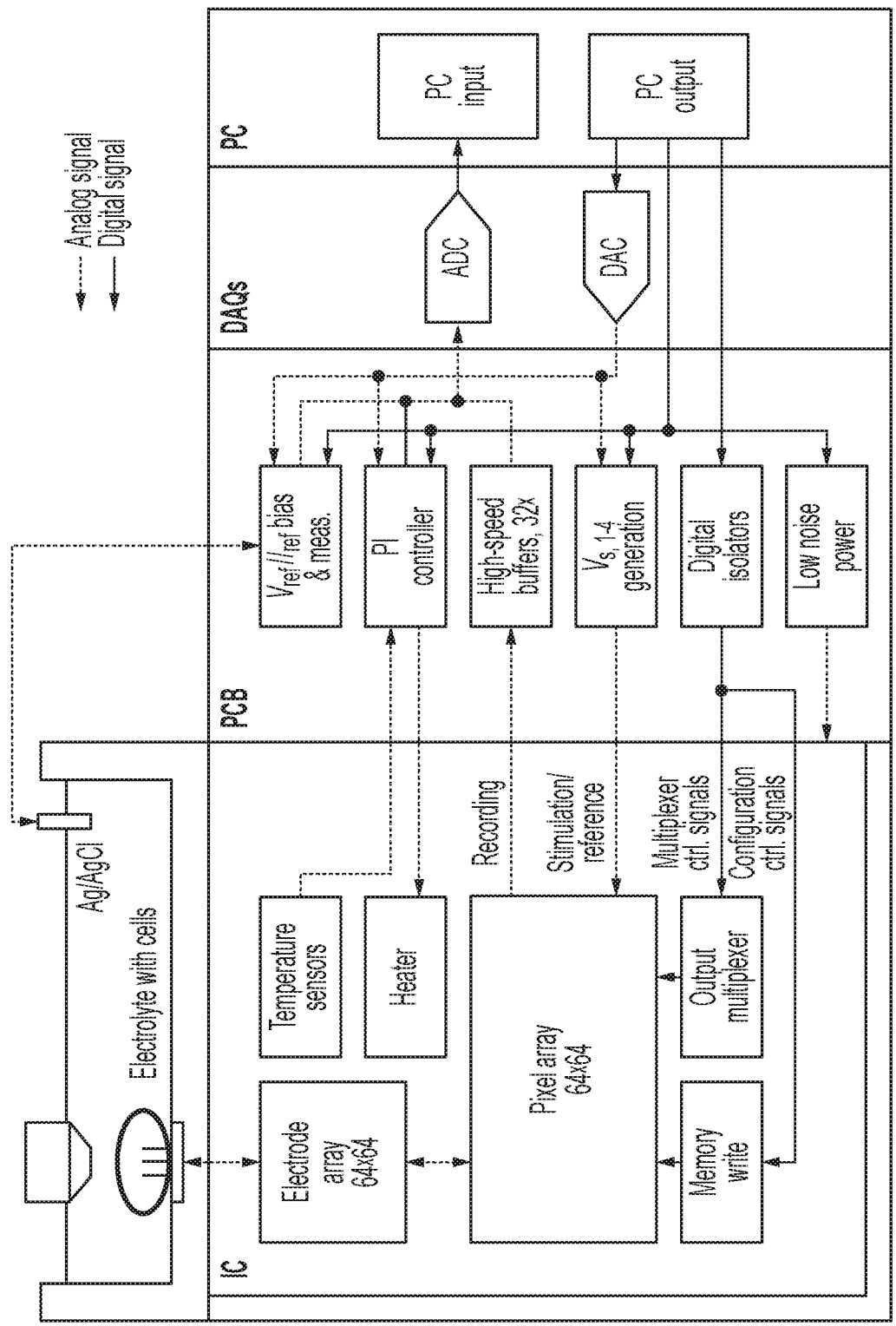
FIG. 12 is a block diagram of a representative test system for characterizing the analyzers described herein, according to some non-limiting embodiments.

FIG. 12 illustrates a representative setup that was used to characterize the analyzers described herein. In one example, the chip (IC) and a printed circuit board (PCB) were programmed and monitored through three National Instruments PXIe-6358 data acquisition (DAQ) cards and interfaced to the user through a real-time custom Labview interface on the personal computer (PC). 4096 amplifier outputs were divided into 32 subgroups, with each containing 128 outputs from 2 rows of the array. The 128 outputs in each subgroup fed a 128:1 analog output multiplexer. This multiplexer was configured to continuously sample the 128 outputs sequentially with a 1.25 MHz clock. Each amplifier output was then sampled at an effective rate of ~9.8 kHz with no aliasing up to ~4.9 kHz. The 128 signals sampled shared the same data line. As a whole, 32 analog output data stream were obtained from the array, which were routed to 32 analog-to-digital converters of the DAQ cards.

The power of the IC was provided by low noise voltage regulators at a fixed voltage of 3.6V. The reference voltages were provided from DAQ card analog outputs and were either low pass filtered to generate a quiet reference voltage or buffered with a bandwidth of ~100 kHz for stimulation. The electrolyte voltage was also controlled using a DAQ card analog output and biased using a Ag/AgCl reference electrode. The voltage of the reference, $V_{ref}$, was either buffered or set using a current measurement circuit; the latter allowed measurement of $I_{ref}$ from ~1 pA to 10 µA with bandwidths of 100 Hz, 1 kHz, or 10 kHz. The reference electrode voltage was adjustable from 0 V to 3.6 V.

The IC also included a heater and temperature sensors. The temperature sensors were differential sensors, using a fixed current but different sized diodes to create a linear output voltage as a function of temperature. The heater was a simple 10Ω-resistor sized to dissipate more than 1.5 W of power. To control the temperature of the IC, and therefore the cells, the temperature signals of the two sensors were averaged and scaled by an analog circuit on the PCB and fed into a PI controller (FIG. 12). The PI controller set the voltage of a regulator able to provide sufficient power for the heater. The time constant, ~30 s, and gain of the PI controller were set very conservatively to avoid oscillation.

Figure 13:
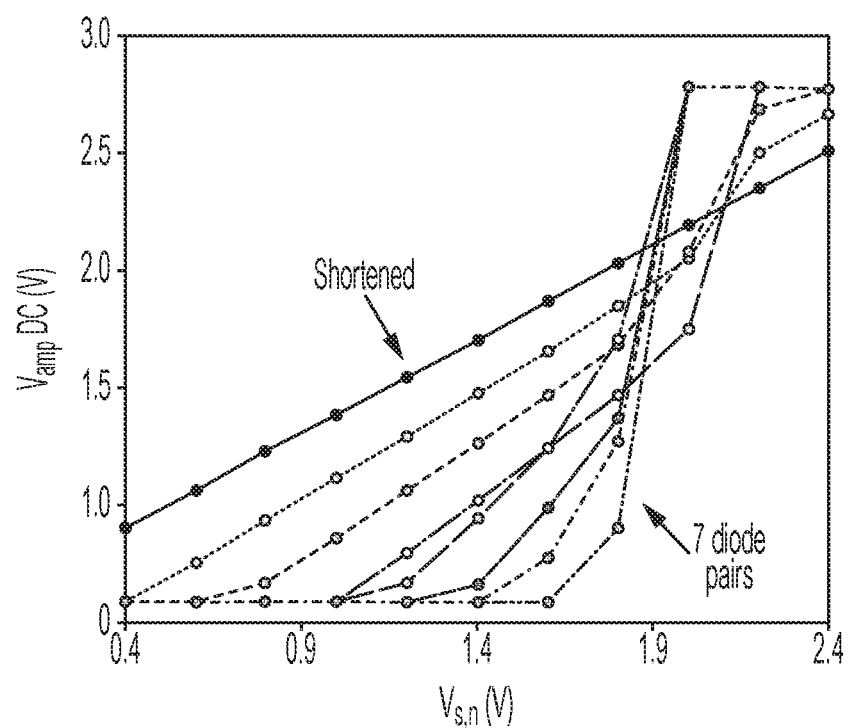
FIG. 13 is a plot illustrating representative experimental results as to how output voltage $V_{amp}$ varies as a function of $V_{s,n}$, according to some non-limiting embodiments.

FIG. 13 illustrates experimental results for the output voltage $V_{amp}$ plotted versus $V_{s,n}$, for a representative 64×64 array. $V_{amp}$ is plotted for various numbers of anti-parallel diode pairs used in $R_{p,2}$ from zero (labelled "shortened" in FIG. 13) to seven. The sharp transition in the median output level for larger number of diode pairs from the upper to lower rails shows the sensitivity of the DC pixel output voltages. The offset voltage due to the leakage current through the diodes scales with increasing number of diode pairs. It is determined that three diode pairs with a $V_{s,n}$=1.8V may offer a reasonable balance between total feedback resistance (proportional to the number of diode pairs and important for the AC low frequency pole) and number of unsaturated pixels.

Figure 14B:
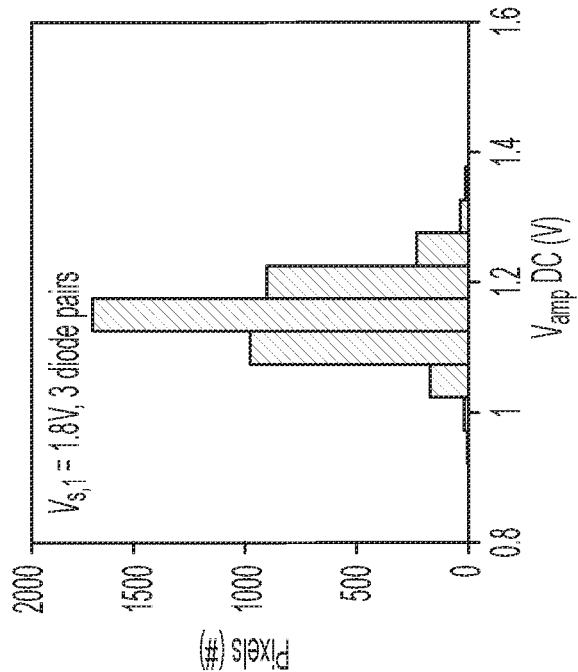
FIG. 14A-14B are plots illustrating representative experimental results for the median gain of a receiver as a function of $V_{s,n}$ and for the distribution of output voltages across a plurality of pixels, respectively, according to some non-limiting embodiments.
Figure 14A:
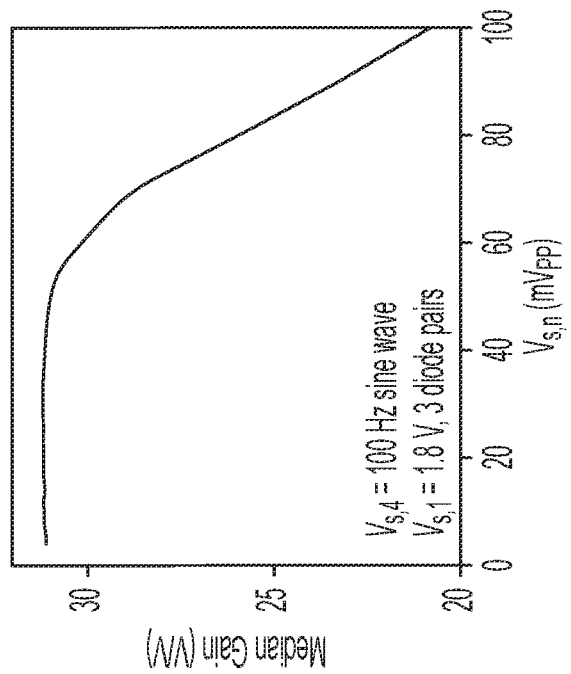

The non-linearity of this configuration is shown in FIG. 14A, where input signals of up to 50 mV can be amplified with a gain of ~30 V/V without distortion. Most importantly, the distribution of the output DC voltage across the 64×64 array (see FIG. 14B) show that all pixels were unsaturated and operational.

Figure 15A:
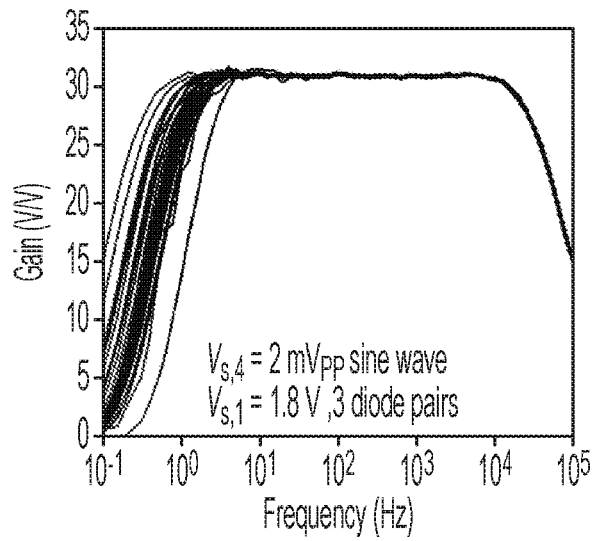
FIGS. 15A-15D are plots illustrating representative experimental results for the gain and noise of various pixels, according to some non-limiting embodiments.
Figure 15B:
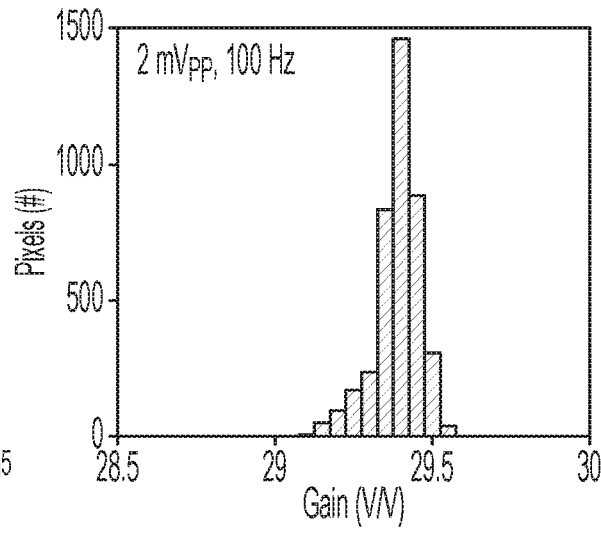
Figure 15C:
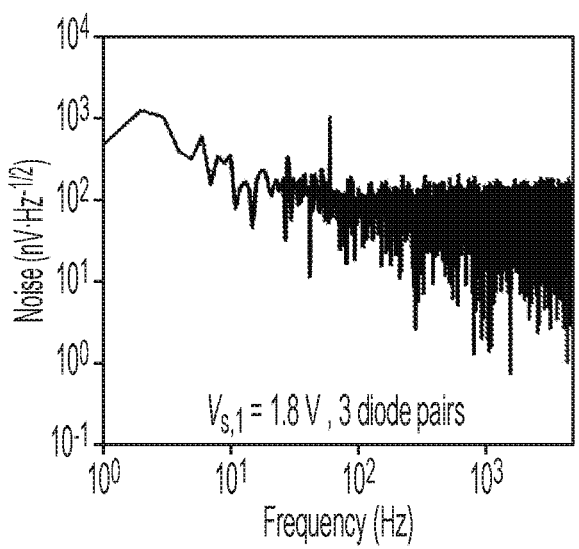
Figure 15D:
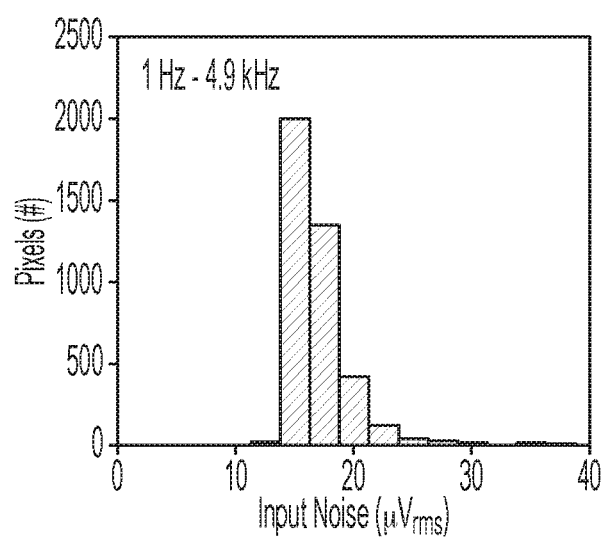

The gain and noise across the device were then characterized, as shown in FIGS. 15A-15D. Gain over frequency plots for 32 pixel amplifiers shows the bandpass nature of the AC coupled configuration, with a low frequency pole ~1 Hz, high frequency pole of ~10 kHz and flat-band gain of ~30 V/V, very close to the desired design values (see FIG. 15A). The distribution of passband gain across the device is very uniform (FIG. 15B). An input noise measurement is shown in FIG. 15C and corresponding integrated RMS noise across the 1 Hz to 4.9 kHz frequency range and across the device is shown in FIG. 15D. The average integrated noise was less than 20 $\mu V_{rms}$, a more than 10× improvement over conventional devices.

Figure 16C:
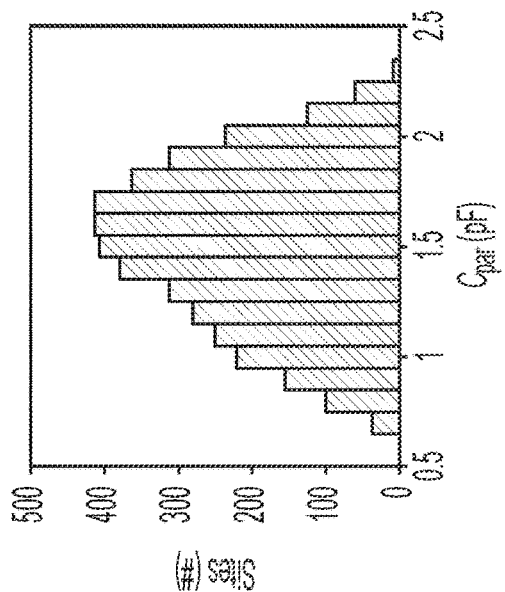
FIGS. 16A-16C are plots illustrating representative experimental results for the parasitic capacitance, according to some non-limiting embodiments.
Figure 16B:
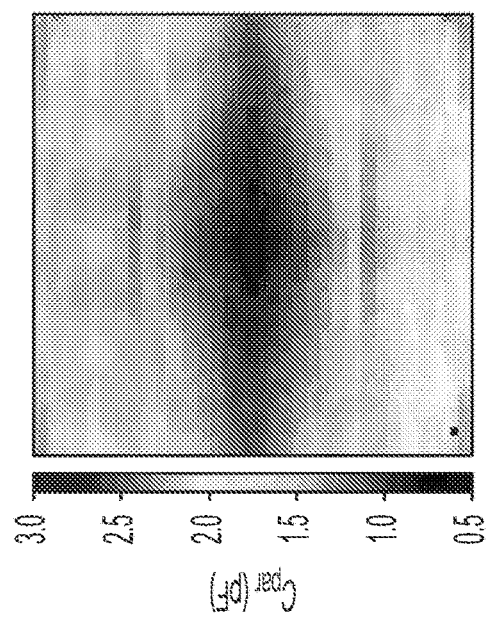
Figure 16A:
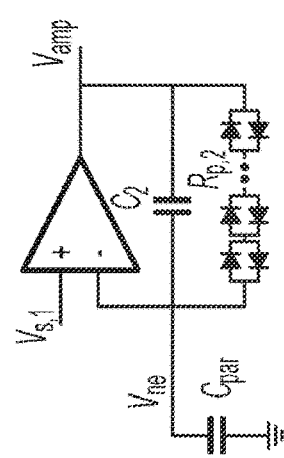

Additionally, the parasitic capacitance of the electrode node due to the wiring between the separated pixel circuitry and the electrode was measured. The results are depicted in FIGS. 16A-16C. The gain from $V_{s,n}$ to $V_{amp}$ was first measured at 100 Hz with $V_{s,n}$ connected to the amplifier's negative terminal through $C_1$ and set to a DC bias. The gain was then measured from $V_{s,n}$ with the amplifier's negative terminal connected to $V_{ne}$ (FIG. 16A). Assuming $C_1$ was its designed value of 3.5 pF, the two gains may be used to calculate the parasitic capacitance of $V_{ne}$, (FIGS. 16B-16C). The parasitic capacitance varied from ~600 fF to ~2 pF depending upon the location of the pixel/electrode and the length of the connection between them. In sum, the separation of the pixel circuitry from the electrode is seen as an effective method to reduce the electrode-to-electrode pitch while maintaining a low-noise pixel circuit.

What is claimed is:

1. An apparatus, comprising:
a plurality of wells, wherein each well comprises an array of electrodes; and
a plurality of analyzers configured to operate in a voltage stimulation mode, wherein each of the plurality of analyzers is coupled to at least one electrode of the array of electrodes, each of the plurality of analyzers comprising an amplifier having a non-inverting input terminal, an inverting input terminal and an output terminal, and a feedback loop, wherein
the inverting input terminal is connected to the at least one electrode such that the at least one electrode, the inverting input terminal, and the non-inverting input terminal have the same voltage,
the feedback loop is disposed between the inverting input terminal and the output terminal such that a current received at the inverting input terminal from the at least one electrode is converted into an output voltage at the output terminal, and
the amplifier is configured to
drive the at least one electrode with a reference voltage; and
convert the current received from the at least one electrode into the output voltage.

2. The apparatus of claim 1, wherein each of at least some of the plurality of analyzers comprises an impedance element coupled between the inverting input terminal of the respective amplifier and the output terminal of the respective amplifier, wherein the impedance element is a tunable switched capacitor.

3. The apparatus of claim 2, wherein the impedance element has an impedance of at least 700 MΩ.

4. The apparatus of claim 3, wherein the impedance element has an impedance of at least 1 GΩ.

5. The apparatus of claim 1, wherein the at least one electrode is covered, at least in part, with a material having a nanoscale roughness.

6. The apparatus of claim 1, wherein the array of electrodes has a pitch that is less than 40 μm.

7. The apparatus of claim 1, further comprising a temperature sensor and a heater disposed adjacent the array of electrodes.

8. The apparatus of claim 1, wherein the at least one electrode is configured to be electrically in contact with a cell.

9. The apparatus of claim 1, wherein the array of electrodes comprises at least 4096 electrodes.

10. The apparatus of claim 1, wherein the array of electrodes is fabricated using complementary metal-oxide-semiconductor techniques.

11. The apparatus of claim 1, wherein the amplifier is fabricated using complementary metal-oxide-semiconductor techniques.

12. The apparatus of claim 1, wherein the plurality of wells comprises at least 96 wells.

13. The apparatus of claim 12, wherein the plurality of wells comprises at least 384 wells.

14. The apparatus of claim 1, wherein the array of electrodes has a pitch less than 30 μm.

15. The apparatus of claim 1, wherein the array of electrodes comprises electrodes comprising iron oxide, aluminum oxide, iridium oxide, tungsten, stainless steel, silver, platinum, gold, aluminum, copper, molybdenum, tantalum, titanium, nickel, tungsten, chromium, or palladium.

16. The apparatus of claim 12, wherein the array of electrodes further comprises a one or more material deposited thereon, the one or more material deposited thereon comprising platinum-black, iridium oxide, gold flakes, carbon nanotubes, silver/silver chloride, or poly(3,4-ethylenedioxythiophene)/poly(styrene sulfonate).

17. The apparatus of claim 1, wherein one or more electrodes of the array of electrodes comprises an outer surface formed of a conductive material.

18. The apparatus of claim 12, wherein
the inverting input terminal is coupled to the at least one electrode via a direct current (DC) connection, and wherein
the amplifier is configured to;
drive the at least one electrode with the reference voltage via the DC connection; and
convert a current received from the at least one electrode via the DC connection into the output voltage.

* * * * *

UNITED STATES PATENT AND TRADEMARK OFFICE
CERTIFICATE OF CORRECTION

| | | |
|---|---|---|
| PATENT NO. | : 12,174,140 B2 | Page 1 of 1 |
| APPLICATION NO. | : 16/760723 | |
| DATED | : December 24, 2024 | |
| INVENTOR(S) | : Donhee Ham et al. | |

It is certified that error appears in the above-identified patent and that said Letters Patent is hereby corrected as shown below:

In the Claims

In Claim 15, at Column 26, Line 22, the text:
"titanium, nickel, tungsten, chromium, or palladium."
Should be replaced with:
-- titanium, nickel, chromium, or palladium. --.

In Claim 16, at Column 26, Line 23, the text:
"The apparatus of claim 12,"
Should be replaced with:
-- The apparatus of claim 1, --.

In Claim 18, at Column 26, Line 32, the text:
"The apparatus of claim 12, wherein"
Should be replaced with:
-- The apparatus of claim 1, wherein --.

Signed and Sealed this
Fourth Day of February, 2025

Coke Morgan Stewart
*Acting Director of the United States Patent and Trademark Office*